United States Patent [19]

Yoshinaga et al.

[11] Patent Number: 4,882,085

[45] Date of Patent: Nov. 21, 1989

[54] LACTIC ACID DERIVATIVE AND LIQUID CRYSTAL COMPOSITION CONTAINING SAME

[75] Inventors: Kazuo Yoshinaga, Machida; Kazuharu Katagiri, Tama; Akira Tsuboyama; Hiroyuki Kitayama, both of Tokyo; Kenji Shinjo, Yokohama; Chieko Hioki, Hiratsuka, all of Japan

[73] Assignee: Canon Kabushiki Kaisha, Tokyo, Japan

[21] Appl. No.: 291,325

[22] Filed: Dec. 28, 1988

Related U.S. Application Data

[63] Continuation of Ser. No. 893,821, Aug. 6, 1986, abandoned.

[30] Foreign Application Priority Data

Aug. 13, 1985 [JP] Japan ................................ 60-176938
Nov. 7, 1985 [JP] Japan ................................ 60-247994
Dec. 28, 1985 [JP] Japan ................................ 60-299003
Jul. 25, 1986 [JP] Japan ................................ 61-173921

[51] Int. Cl.[4] ...................... C09K 19/12; C09K 19/34; C09K 19/20; G02F 1/13
[52] U.S. Cl. .......................... 252/299.61; 252/299.01; 252/299.65; 252/299.67; 350/350 S; 560/59; 560/66; 560/73; 560/86; 560/102; 560/108; 560/109; 544/298; 544/335
[58] Field of Search ................ 252/299.01, 299.65, 252/299.67, 299.61; 350/350 S; 560/59, 66, 73, 86, 102, 108, 109

[56] References Cited

U.S. PATENT DOCUMENTS

| | | | |
|---|---|---|---|
| 4,556,727 | 12/1985 | Walba | 252/299.67 |
| 4,576,732 | 3/1986 | Isogai et al. | 252/299.65 |
| 4,596,667 | 6/1986 | Inukai et al. | 252/299.65 |
| 4,638,073 | 1/1987 | Walba et al. | 252/299.67 |
| 4,650,600 | 3/1987 | Heppke et al. | 252/299.01 |
| 4,725,688 | 2/1988 | Taguchi et al. | 252/299.01 |
| 4,744,918 | 5/1988 | Heppke et al. | 252/299.65 |
| 4,775,223 | 10/1988 | Yoshinaga et al. | 252/299.01 |
| 4,812,259 | 3/1989 | Yoshinaga et al. | 252/299.65 |

FOREIGN PATENT DOCUMENTS

| | | | |
|---|---|---|---|
| 175591 | 3/1986 | European Pat. Off. | 252/299.65 |
| 82/176267 | 10/1982 | Japan | 252/299.01 |
| 86/02937 | 5/1986 | World Int. Prop. O. | 252/299.65 |
| 86/02938 | 5/1986 | World Int. Prop. O. | 252/299.65 |

OTHER PUBLICATIONS

GRUR 1983, p. 434, "Polymerisierbares Gemisch".

Primary Examiner—John F. Terapane
Assistant Examiner—J. E. Thomas
Attorney, Agent, or Firm—Fitzpatrick, Cella, Harper & Scinto

[57] ABSTRACT

An optically active lactic acid derivative represented by the following formula (I):

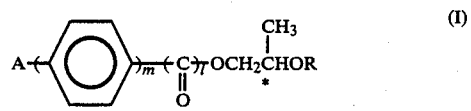

wherein R represents a linear, branched or cyclic saturated or unsaturated hydrocarbon group having 1 to 18 carbon atoms; C* represents an asymmetric carbon atom; l is 0 or 1; m is 1 or 2; A represents a group selected from the following groups (a) and (b):

(a) hydroxyl group, halogen, benzyloxy group, phenoxy group, toluenesulfonic acid group, acetyloxy group trifluoroacetyloxy group;

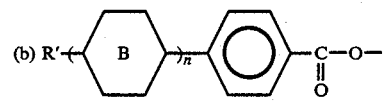

(wherein R' is an alkyl group or alkoxy group having 4 to 18 carbon atoms, n is 0 or 1, (Abstract continued on next page.)

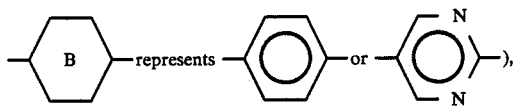
with proviso that when A is selected from the group in the above group (a), l is 1 and m is 1 or 2; and when A is selected from the groups in the above group (b), m=n=1 when l is 0, or m and n are 0, 1 or 2 and m+n is 1 or 2 when l is 1, and
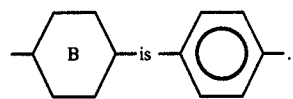
20 Claims, 5 Drawing Sheets

LACTIC ACID DERIVATIVE AND LIQUID CRYSTAL COMPOSITION CONTAINING SAME

This application is a continuation of application Ser. No. 893,821, filed August 6, 1986 now abandoned.

FIELD OF THE INVENTION AND RELATED ART

The present invention relates to a lactic acid derivative capable of being readily modified with respect to its molecular structure and having an optical activity, and a composition containing the lactic acid derivative. More specifically, the present invention relates to an intermediate of a mesomorphic compound which is an optically active lactic acid derivative, a mesomorphic compound derived therefrom and a liquid crystal composition containing the same, and also to a liquid crystal device using the liquid crystal composition.

There are well known types of liquid crystal devices using TN (twisted nematic) type liquid crystals shown, for example, in "Voltage-Dependent Optical Activity of a Twisted Nematic Liquid Crystal" by M. Schadt and W. Helfrich, Applied Physics Letters, Vol. 18, No. 4 (Feb. 15, 1971) pp. 127-128. In this type of liquid crystal device, the number of picture elements have been restricted, because there is a problem that a crosstalk phenomenon occurs when a device of a matrix electrode structure with a high density of picture elements is driven according to a time-sharing of time-division driving scheme. Further, their uses for display have been limited because of slow electric field response and poor visual angle characteristics.

As another type of liquid crystal device, there is known one comprising a plurality of picture elements each connected to and subject to switching by a thin film transistor switching element. This type of liquid crystal device, however, is accompanied with problems such that production of thin film transistors on a substrate is very complicated, and production of a display device with a large picture area or screen is difficult.

In order to obviate the above-mentioned drawbacks of the conventional types of liquid crystal devices, Clark and Lagerwall have proposed the use of a liquid crystal device wherein a ferroelectric liquid crystal is disposed in a thin layer having a thickness less than 5 times that of the spiral pitch thereof so that its spiral structure is unwound to develop a bistability (e.g., U.S. Pat. No. 4367924).

As the bistable liquid crystal, a ferroelectric crystal showing a chiral smectic C phase (SmC*) or H phase (SmH*) is generally used.

Such a ferroelectric liquid crystal has a rapid response speed on account of having spontaneous polarization, can exhibit memorizable bistable state and further has an excellent vision angle characteristic, and therefore it is suitable for a display of large capacity and picture area.

The mesomorphic compound which is used for ferroelectric liquid crystal has an asymmetric carbon and therefore can be used for optical devices as shown below other than the utilization for a ferroelectric liquid crystal in which its chiral smectic phase is used:

(1) the device in which cholesteric-nematic phase transition effect is utilized in mesomorphic state (J. J. Wysoki, A. Adams and W. Haas; Phys. Rev. Lett., 20, 1024 (1968));

(2) the device in which White-Taylor type guest-host effect is utilized (D. L. White and G. N. Taylor; J. Appl. Phys., 45, 4718 (1974));

(3) the device in which a compound having cholesteric phase in mesomorphic state is fixed in matrix and utilized as notch filter or band bath filter by utilizing its selective scattering characteristics (F. J. Kahn, Appl. Phys. Lett., 18, 231 (1971)), or the device in which the compound is utilized as a circular polarizing light beam splitter by utilizing the circular polarizing light characteristic (S. D. Jacobs, SPIE, 37, 98 (1981)); etc.

Although detailed descriptions of the individual systems are omitted here, each are important as display or modulating devices.

In the prior art, as the optically active intermeidate for synthesis for functional materials necessary for optical devices characterized by having optical activity, 2-methylbutanol, sec-octyl alcohol, sec-butyl alcohol, p-(2-methylbutyl)benzoic acid chloride, sec-phenetyl alcohol, amino acid derivatives, camphor derivatives, and cholesterol derivatives have been known.

However, these compounds have the following drawbacks. Optically active chain hydrocarbon derivatives can be modified in structure only with difficulty, and they are generally very expensive except for a particular class thereof. Amino acid derivatives are relatively inexpensive and are also modified in structure with ease, but the hydrogen atom of amine has strong chemical activity to readily form hydrogen bond or cause chemical reaction, whereby the characteristics of the functional material are liable to be restricted. Camphor derivatives and cholesterol derivatives can be modified in structure with difficulty and also affect badly the characteristics of functional materials due to their steric hindrances.

The drawbacks mentioned above have previously been great restrictions in developments of various materials.

SUMMARY OF THE INVENTION

In view of the state of the art as described above, a principal object of the present invention is to provide an optically active compound which is not only useful as a suitable optically active intermediate but also useful for control of mesomorphic state, and also a liquid crystal composition containing the same.

More specifically, an object of the present invention is to provide a compound which can be combined with an intermediate for a functional material having appropriate intermolecular force and shape for forming liquid crystal, LB (Langmuir-Blodgett) film, bi-molecular films, etc., without impairing an optical activity, and therefore susceptible of arbitrary molecular designing. Another object of the present invention is to provide a compound which undergoes great spontaneous polarization when used as a ferroelectric liquid crystal due to the presence of an oxygen atom adjacent to an asymmetric carbon atom.

Still another object of the present invention is to provide a mesomorphic compound capable of readily changing the length of the alkyl chain and therefore capable of controlling a kind of liquid crystal phase to be developed in the liquid crystal state and a temperature range therefor as shown by H. Arnold, Z. Phys. Chem., 226, 146 (1964), and a liquid crystal composition containing at least one of such mesomorphic compounds.

A further object of the present invention is to provide a compound capable of easily controlling the hydrophobic group and being stably formed into a film when applied to the LB (Langmuir-Blodgett) film process for preparing built-up monomolecular films.

More specifically, the present invention provides an optically active lactic acid derivative represented by the following formula (I):

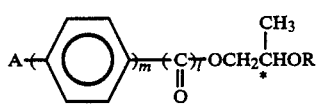 (I)

wherein R represents a linear, branched or cyclic saturated or unsaturated hydrocarbon group having 1 to 18 carbon atoms; C* represents an asymmetric carbon atoms; l is 0 or 1; m is 1 or 2; A represents a group selected from the following groups (a) and (b):

(a) hydroxy group, halogen, benzyloxy group, phenoxy group, toluenesulfonic acid group, acetyloxy group, trifluoroacetyloxy group; and (b)

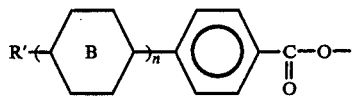

(wherein R' is an alkyl group or alkoxy group having 4 to 18 carbon atoms, n is 0 or 1,

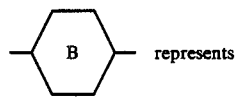 represents

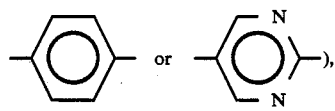

with proviso that when A is selected from the groups in the above group (a), l is 1 and m is 1 or 2, or when A is selected from the groups in the above group (b), m=n=1 when l is 0, or m and n are 0, 1 or 2 and m+n is 1 or 2 when l is 1, and

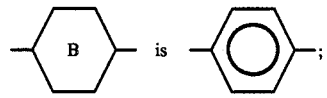

and a liquid crystal composition containing at least one of such compounds.

DETAILED DESCRIPTION OF THE INVENTION

Figure 1:
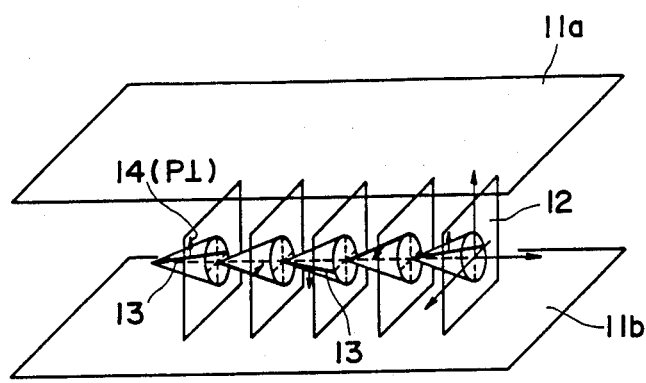
FIGS. 1 and 2 are perspective views representing schematically the liquid crystal device for time-division driving to be used in the present invention.

In the formula (I) representing the above optically active substance, R is a linear, branched or cyclic saturated or unsaturated hydrocarbon group having 1 to 18 carbon atoms. A group having 19 or more carbon atoms is not preferable because the viscosity or molar volume of the functional material finally made will be increased. A more preferable carbon number of R is 4 to 16. Typical examples of R include linear alkyl group, branched alkyl group, cycloalkyl group, linear alkenyl group, branched alkenyl group, cycloalkenyl group, linear alkadienyl group, branched alkadienyl group, cycloalkadienyl group, linear alkatrienyl group, branched alkatrienyl group, linear alkynyl group, branched alkynyl group, and aralkyl group. For providing mesomorphic compounds as described below, alkyl groups are particularly preferred. C* represents an asymmetric carbon atom.

Of the lactic acid derivatives of the present invention, preferable examples may include the lactic acid derivatives represented by the following formula (III):

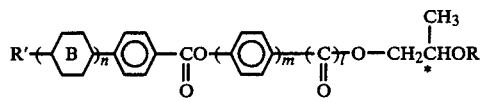

wherein R represents a linear, branched or cyclic saturated or unsaturated hydrocarbon group having 1 to 18 carbon atoms; C* represents an asymmetric carbon atom; R' represents an alkyl group or alkoxy group having 4 to 18 carbon atoms; l is 0 or 1; m is 1 or 2, n is 0 or 1; and

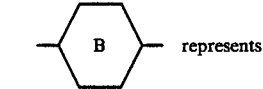 represents

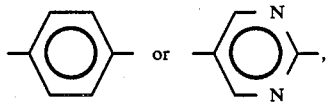

with proviso that m=n=1 when l is 0, or m and n are 0, 1 or 2 and m+n is 1 or 2 when l is 1.

Further, in the present invention of the lactic acid derivatives of the above formula (III), the lactic acid derivatives corresponding to those wherein l is 1 can be derived from the lactic acid derivatives represented by the following formula (II):

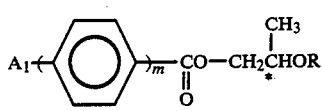

(II)

wherein R represents a linear, branched or cyclic saturated or unsaturated hydrocarbon group; C* represents an asymmetric carbon atom; m is 1 or 2; and $A_1$ represents a releasable substituent selected from hydroxyl group, halogen, benzyloxy group, phenoxy group, toluenesulfonic acid group, acetyloxy group and trifluoroacetyloxy group, which can be substituted with other groups through the reaction with a reaction reagent under appropriate conditions. In this case, by varying variously the reaction reagents, mesomorphic compounds and other functional compounds can be obtained.

As examples of such mesomorphic compounds, there are compounds wherein $A_1$ is

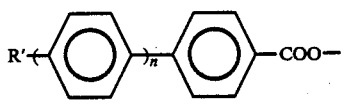

(wherein R' is an alkyl group or an alkoxy group having 4 to 18 carbon atoms, and n is 0 or 1) (represented by the formula (V)). In this case, the particularly preferable carbon number in R' is 6 to 16. Formula (V):

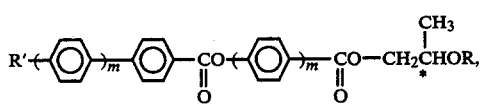

(V)

wherein R represents a linear, branched or cyclic saturated or unsaturated hydrocarbon groups having 1 to 18 carbon atoms; C* represents an asymmetric carbon atom; R' represents an alkyl group or alkoxy group having 4 to 18 carbon atoms; m is 1 or 2, and n is 0 or 1.

In order to synthesize functional materials adapted for use in optical devices, modulation devices, etc., it is effective to combine the optically active lactic acid derivative without impairing the optical activity with an intermediate of functional material having an appropriate intermolecular force and shape and susceptible of molecular control. Examples of such intermediates of functional material effective for combination with the lactic acid derivative according to the present invention include azo derivatives, azoxy derivatives, ring-assembly hydrocarbon derivatives, condensed polycyclic hydrocarbon derivatives, heterocyclic derivatives, condensed heterocyclic derivatives, and ring-assembly heterocyclic derivatives. More specifically, there are included azobenzene derivatives, azoxybenzene derivatives, biphenyl derivatives, terphenyl derivatives, phenylcyclohexane derivatives, benzoic acid derivatives pyrimidine derivatives, pyrazine derivatives, pyridine derivatives, stilbene derivatives, tolan derivatives, chalcone derivatives, bicyclohexane derivatives, and cinnamic acid derivatives.

In the following is explained a process of synthesizing a compound having a releasable chemically active group $A_1$ as an example of the actic acid derivatives shown by the formula (I) according to the present invention:

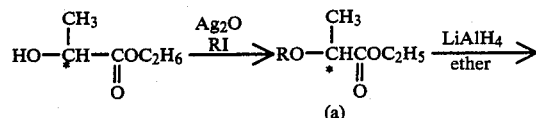

(a)

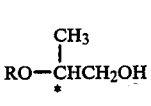

(b)

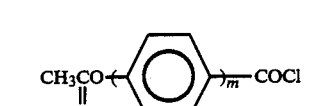

(b) →

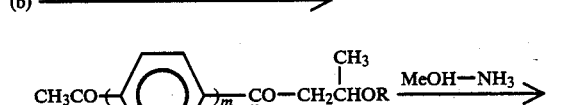

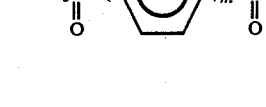

(c)

(c) →

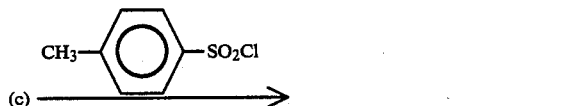

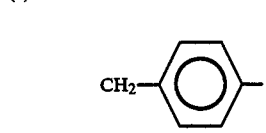

(d) $\xrightarrow{(CF_3CO)_2O}$ 

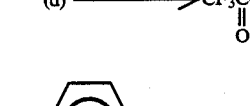

(c) →

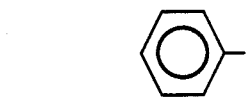

(b) →

($A_1$ = F, Cl, Br, I)

The RI in the above reaction scheme may be selected from a wide scope of iodides. Examples thereof include linear saturated hydrocarbon iodides such as iodobutane, iodopentane, iodohexane, iodoheptane, iodooctane, iodononane, iododecane, iodoundecane, iodododecane, iodotridecane, iodotetradecane, iodopentadecane, iodohexadecane, iodoheptadecane, iodooctadecane, iodononadecane, and iodocicosane; branched saturated hydrocarbon iodides such as 2-iodobutane, 2-iodo-2-methylpropane and 1-iodo-3-methylbutane; cyclic unsaturated hydrocarbon iodides such as iodobenzyl, iodophenacyl and 3-iodo-1-cyclohexene; and cyclic saturated hydrocarbon iodides such as iodocyclopentane, iodocyclohexane, 1-iodo-3-methylcyclohexane, iodocycloheptane and iodocyclooctane.

An appropriate RI may be selected from the iodides as described above to obtain an optically active lactic acid derivative according to the present invention. Optical rotation data of some examples of the optically active lactic acid derivatives obtained from the linear saturated hydrocarbon iodides are shown in the following Table 1.

TABLE 1

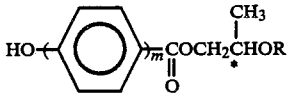

| Example | R | m | $[\alpha]_D$ |
|---|---|---|---|
| 1 | $C_2H_5-$ | 1 | +13.0° |
| 2 | $n-C_3H_7-$ | 1 | +7.6° |
| 3 | $n-C_5H_{11}-$ | 1 | +10.3° |
| 4 | $n-C_8H_{17}-$ | 1 | +7.3° |
| 5 | $n-C_{12}H_{25}-$ | 1 | +6.0° |
| 6 | $n-C_5H_{11}-$ | 2 | +6.3° |

By using various lactic acid derivatives obtained in the manner as described above, mesomorphic compounds shown below were obtained along the following reaction scheme.

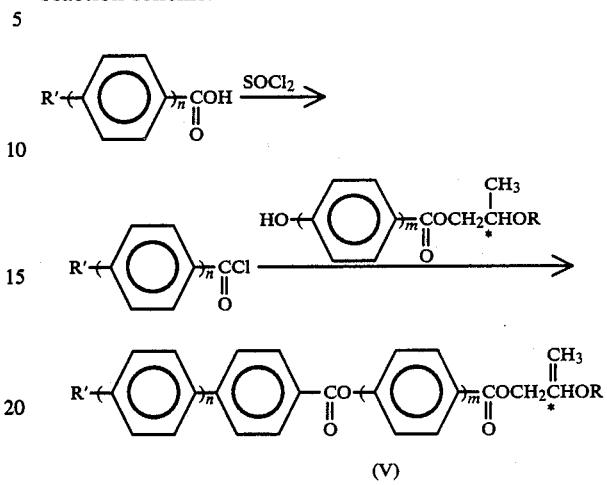

(V)

(in the above formulae, R, R′, m and n are as defined above).

Table 2 shows examples of the mesomorphic lactic acid derivatives thus obtained.

TABLE 2

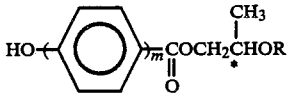

| Example | R | R′ | n | m | Phase transition temperature (°C.) |
|---|---|---|---|---|---|
| 7 | $C_2H_5-$ | $n-C_8H_{17}O-$ | 1 | 1 | Cryst. $\xrightarrow{78}$ SmC* $\underset{126}{\overset{129}{\rightleftarrows}}$ SmA $\underset{177}{\overset{180}{\rightleftarrows}}$ Iso.  $31\searrow \nearrow 49$  Sm1 |
| 8 | $n-C_3H_7-$ | $n-C_8H_{17}O-$ | 1 | 1 | Cryst. $\xrightarrow{81}$ SmC* $\underset{119}{\overset{123}{\rightleftarrows}}$ SmA $\underset{169}{\overset{172}{\rightleftarrows}}$ Iso.  $33\searrow \nearrow 46$  Sm1 |
| 9 | $C_2H_5-$ | $n-C_{10}H_{21}O-$ | 1 | 1 | Cryst. $\xrightarrow{77}$ SmC* $\underset{134}{\overset{137}{\rightleftarrows}}$ SmA $\underset{174}{\overset{177}{\rightleftarrows}}$ Iso.  $32\searrow \nearrow 41$  Sm1 |
| 10 | $n-C_3H_7-$ | $n-C_{10}H_{21}O-$ | 1 | 1 | Cryst. $\underset{34}{\overset{79}{\rightleftarrows}}$ SmC* $\underset{132}{\overset{135}{\rightleftarrows}}$ SmA $\underset{167}{\overset{170}{\rightleftarrows}}$ Iso. |
| 11 | $n-C_{12}H_{25}-$ | $n-C_5H_{11}O-$ | 1 | 1 | Cryst. $\xrightarrow{89}$ SmA $\underset{153}{\overset{156}{\rightleftarrows}}$ Iso.  $61\searrow \nearrow 71$  Sm2 $\xleftarrow{66}$ Sm1 |
| 12 | $n-C_{12}H_{25}-$ | $n-C_{12}H_{25}O-$ | 1 | 1 | Cryst. $\underset{50}{\overset{83}{\rightleftarrows}}$ SmC* $\underset{93}{\overset{95}{\rightleftarrows}}$ SmA $\underset{136}{\overset{139}{\rightleftarrows}}$ Iso. |

TABLE 2-continued $$R'{-}{\bigcirc}_n{-}{\bigcirc}{-}COO{-}({\bigcirc})_m{-}COOCH_2\overset{*}{C}HOR\text{ (}CH_3\text{)}$$

| Example | R | R' | n | m | Phase transition temperature (°C) |
|---------|---|----|----|----|-----------------------------------|
| 13 | n-C$_8$H$_{17}$— | n-C$_8$H$_{17}$O— | 1 | 1 | Cryst. ⇌68/38 Sm1 ⇌48 Sm2; Sm1 ⇌112/109 SmA ⇌155/152 Iso. |
| 14 | n-C$_5$H$_{11}$— | n-C$_{16}$H$_{33}$O— | 1 | 1 | Cryst. ⇌92/70 SmC* ⇌119/117 SmA ⇌149/147 Iso. |
| 15 | n-C$_8$H$_{17}$— | n-C$_7$H$_{15}$— | 1 | 1 | Cryst. ⇌68/32 Sm1 ⇌94/91 SmA ⇌123/120 Iso. |
| 19 | n-C$_5$H$_{11}$— | n-C$_{12}$H$_{25}$O— | 0 | 1 | Cryst. ⇌42/13 SmA ⇌47/43 Iso. |
| 20 | n-C$_5$H$_{11}$— | n-C$_{10}$H$_{21}$O— | 0 | 2 | Cryst. ⇌55/14 Sm1 ⇌30 SmC*; SmC* ⇌94/91 SmA ⇌143/143 Iso. |

In the above Table and the description appearing hereinafter the abbreviations used for describing phase transition characteristics represent the following:
Cryst.: crystalline phase
Ch.: cholesteric phase
Iso.: isotropic phase
SmC*: chiral smectic phase
SmA: smectic A phase
SmB: smectic B phase
SmC: smectic C phase
N: nematic phase
Sm1, Sm2, Sm3: smectic phase (unidentified)

The liquid crystal composition of the present invention contains an optically active substance or mesomorphic lactic acid derivative represented by the above formula (V) as at least one component.

Of the above compositions, those containing ferroelectric liquid crystals as represented by the following formula A-(1) to A-(13) can increase spontaneous polarization and further improve response speed together with the effect of lowering viscosity, and therefore preferred. In such a case, it is preferable to use an otically active lactic acid derivative of the present invention represented by the formula (V) at a proportion of 0.1 to 30 wt.%, and a mesomorphic lactic acid derivative of the present invention represented by the formula (V) should preferably be used at a proportion of 0.1 to 99 wt.%, particularly 1 to 90 wt.%.

A-(1)

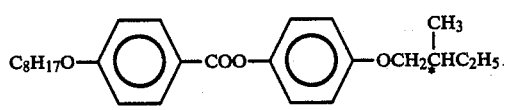

4'-(2-methylbutyloxy)phenyl-4-octyloxy-benzoate

Cryst. →42° C.→ SmC* →43.5° C.→ SmA →58.5° C.→ Ch. →62° C.→ Iso.

A-(2)

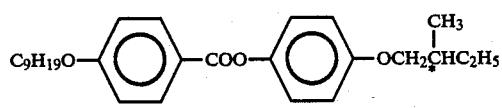

4'-(2-methylbutyloxy)phenyl 4-nonyloxy-benzoate

Cryst. →44→ SmA →60→ Iso.
          ↘43.5
        SmC*

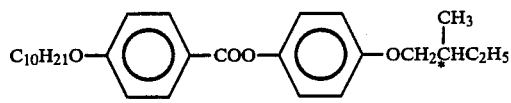    A-(3)

4'-(2-methylbutyloxy)phenyl 4-decyloxybenzoate

Cryst. $\xrightarrow{44}$ SmC* $\xrightarrow{50}$ SmA $\xrightarrow{65}$ Iso.

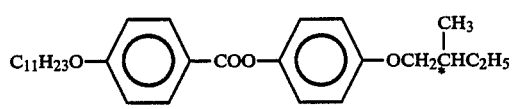    A-(4)

4'-(2-methylbutyloxy)phenyl 4-undecyloxy-benzoate

Cryst. $\xrightarrow{49.5}$ SmA $\xrightarrow{63}$ Iso.
$\searrow 48$
SmC*

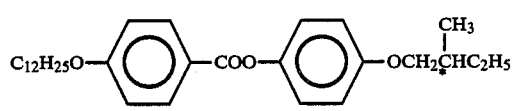    A-(5)

4'-(2-methylbutyloxy)phenyl 4-dodecyloxy-benzoate

Cryst. $\xrightarrow{49}$ SmC* $\xrightarrow{52}$ SmA $\xrightarrow{65}$ Iso.

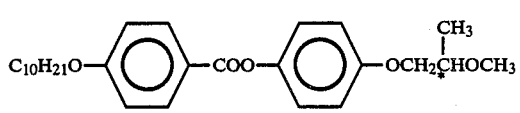    A-(6)

4'-(2-methoxypropyloxy)phenyl 4-decyloxy-benzoate

Cryst. $\xrightarrow{40}$ SmA $\xrightarrow{47}$ Iso.
$\nwarrow 17 \quad \swarrow 23$
Sm1 $\longleftarrow$ SmC*

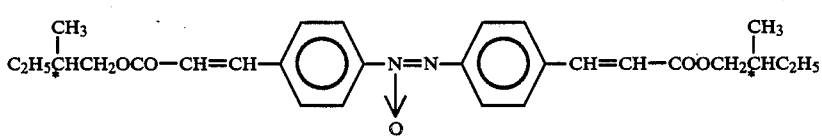    A-(7)

4,4'-azoxycinnamic acid-bis(2-methylbutyl)-ester

Cryst. $\underset{\rightleftarrows}{\xrightarrow{121}}$ SmC* $\underset{\rightleftarrows}{\xrightarrow{134}}$ SmA $\underset{\rightleftarrows}{\xrightarrow{168}}$ Iso.

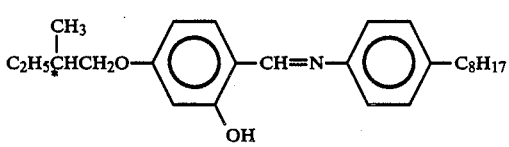    A-(8)

4-o-(2-methyl)-butylresorcylidene-4'-octylaniline

Cryst. $\underset{\rightleftarrows}{\xrightarrow{280}}$ SmC* $\underset{\rightleftarrows}{\xrightarrow{55}}$ SmA $\underset{\rightleftarrows}{\xrightarrow{62}}$ Iso.

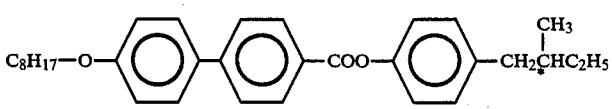    A-(9)

4-(2'-methylbutyl)phenyl-4'-octyloxybiphenyl-4-carboxylate

A-(10)

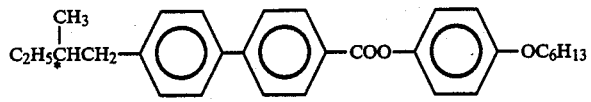

4-hexyloxyphenyl-4-(2''-methylbutyl)biphenyl-4-carboxylate

A-(11)

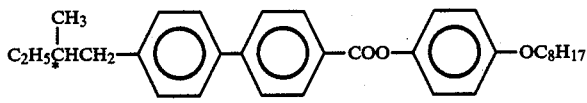

4-octyloxyphenyl-4-(2''-methylbutyl)biphenyl-4'-carboxylate

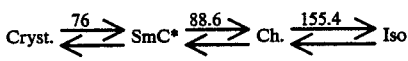

A-(12)

4-heptylphenyl-4-(4''-methylhexyl)carboxylate

A-(13)

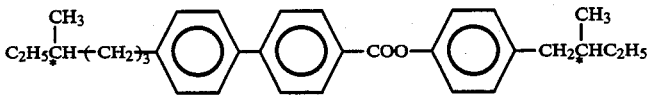

4-(2''-methylbutyl)phenyl-4-(4''-methylhexyl)biphenyl-4'-carboxylate

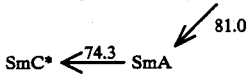

Also, by formulating into a smectic liquid crystal which is not itself chiral as represented by the following formulae B-(1) to B-(5), a composition utilizable as ferroelectric liquid crystal can be obtained.

In such a case, the optically active substance which is the lactic acid derivative represented by the formula (V) can be used at a proportion of 0.1 to 90 wt.%. Also, the mesomorphic lactic acid derivative of the present invention represented by the formula (V) can be used at a proportion of 0.1 to 99 wt.%.

B-(1)

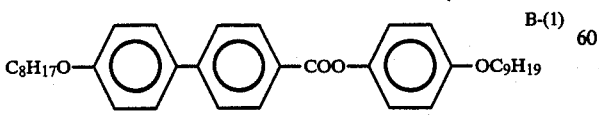

(4-nonyloxyphenyl)-4'-octyloxybiphenyl-4-carboxylate

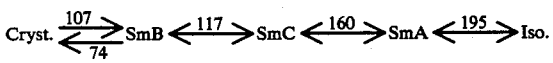

-continued

B-(2)

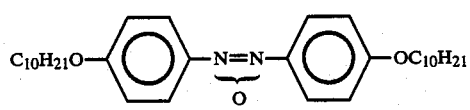

4,4'-decyloxyazoxybenzene

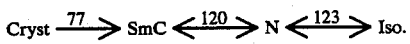

B-(3)

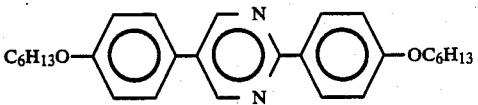

2-(4'-hexyloxyphenyl)-5-(4'-hexyloxyphenyl)-pyrimidine

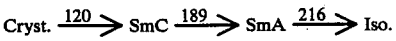

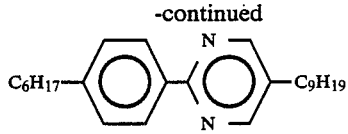

2-(4'-octyloxyphenyl)-5-nonylpyrimidine

Cryst. $\xrightarrow{33}$ SmC $\xrightarrow{60}$ SmA $\xrightarrow{75}$ Iso.

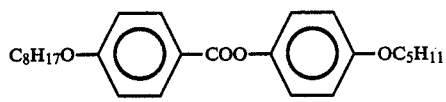

4'-pentyloxyphenyl-4-octyloxybenzoate

Cryst. $\xrightarrow{58}$ SmC $\xrightarrow{64}$ SmA $\xrightarrow{66}$ N $\xrightarrow{85}$ Iso.

Also, the nematic liquid crystal containing the lactic acid derivative of the present invention as at least one formulation component can be preferably used in the form of a twisted nematic (TN) type cell, whereby generation of reverse domain can be prevented.

On the other hand, of the lactic acid derivatives represented by the above formula (III), the lactic acid derivatives corresponding to those wherein l is 0 can be derived from the lactic acid derivatives of the following formula (VI):

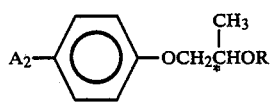 (VI)

wherein R represents a linear, branched or cyclic saturated or unsaturated hydrocarbon group having 1 to 18 carbon atoms; C* represents an asymmetric carbon atom; and $A_2$ represents a chemically active substituent.

$A_2$ represents a releasable chemically active substituent such as a halogen atom, alkoxy group, phenoxy group, toluenesulfonic acid group, thiol group, etc. That is, R can be easily substituted with another group through the reaction with a reaction reagent and appropriate reaction conditions. In this case, by varying variously the reaction reagent, mesomorphic compounds and other functional compounds can be obtained. Examples of effective intermediate of functional material for combination with the lactic acid derivative include azo derivatives, azoxy derivatives, ring-assembly hydrocarbon derivatives, condensed polycyclic hydrocarbon derivatives, heterocyclic derivatives, condensed heterocyclic derivatives, and ring-assembly heterocyclic derivatives. More specifically, there are included azobenzene derivatives, azoxybenzene derivatives, biphenyl derivatives, terphenyl derivatives, phenylcyclohexane derivatives, benzoic acid derivatives, pyrimidine derivatives, pyradine derivatives, pyridine derivatives, stilbene derivatives, tolan derivatives, chalcone derivatives, bicyclohexane derivatives, and cinnamic acid derivatives.

In the following is explained a process of synthesizing a compound having a releasable chemically active group $A_2$ as an example of the lactic acid derivative shown by the formula (I) according to the present invention:

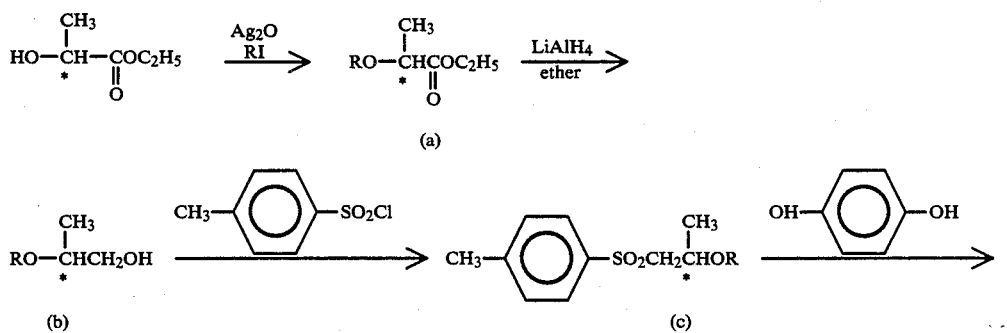

-continued

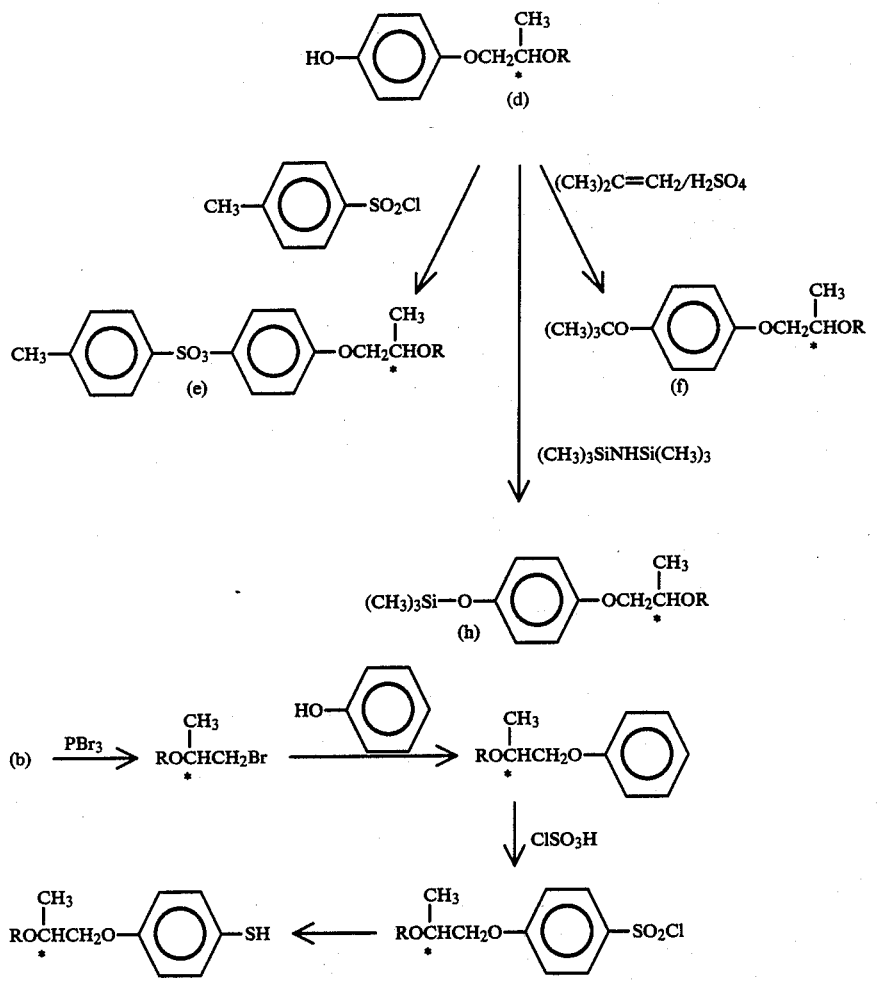

The RI in the above reaction scheme may be selected from a wide scope of iodides. Examples thereof include linear saturated hydrocarbon iodides such as iodobutane, iodopentane, iodohexane, iodoheptane, iodooctane, iodononane, iododecane, iodoundecane, iodododecane, iodotridecane, iodotetradecane, iodopentadecane, iodohexadecane, iodoheptadecane, iodooctadecane, iodononadecane, and iodocicosane; branched saturated hydrocarbon iodides such as 2-iodobutane, 2-iodo-2-methylpropane and 1-iodo-3-methylbutane; cyclic unsaturated hydrocarbon iodides such as iodobenzyl, iodophenacyl and 3-iodo-1-cyclohexene; and cyclic saturated hydrocarbon iodides such as iodocyclopentane, iodocyclohexane, 1-iodo-3-methylcyclohexane, iodocycloheptane and iodocyclooctane.

An appropriate RI may be selected from the iodides as described above to obtain an optically active lactic acid derivative according to the present invention. Optical rotation data of some examples of the optically active lactic acid derivatives obtained from the linear saturated hydrocarbon iodides are shown in the following Table 3.

TABLE 3

$$R-O-\overset{CH_3}{\underset{*}{C}}HCH_2O-\phantom{a}\text{—}\phantom{a}OH$$

| R | Optical Rotation | Example |
|---|---|---|
| $C_4H_9-$ | $-14.1°$ | 22 |
| $C_5H_{11}-$ | $-13.5°$ | 23 |
| $C_6H_{13}-$ | $-12.5°$ | 27 |
| $C_7H_{15}-$ | $-12.0°$ | 28 |
| $C_8H_{17}-$ | $-11.3°$ | 24 |
| $C_9H_{19}-$ | $-10.6°$ | 29 |
| $C_{10}H_{21}-$ | $-10.0°$ | 30 |
| $C_{11}H_{23}-$ | $-9.3°$ | 31 |
| $C_{12}H_{25}-$ | $-8.6°$ | 25 |
| $C_{13}H_{27}-$ | $-7.9°$ | 32 |
| $C_{14}H_{29}-$ | $-7.2°$ | 33 |
| $C_{15}H_{31}-$ | $-6.5°$ | 34 |
| $C_{16}H_{33}-$ | $-5.9°$ | 35 |
| $C_{17}H_{35}-$ | $-5.3°$ | 36 |
| $C_{18}H_{37}-$ | $-5.0°$ | 26 |
| $CH_3-$ | $-16°$ | 37 |
| $C_2H_5-$ | $-14.7°$ | 38 |
| $C_3H_7-$ | $-15.5°$ | 39 |

From the various lactic acid derivatives obtained according to such a process, mesomorphic compounds represented by the following formula (IV) were obtained along the synthetic route shown below.

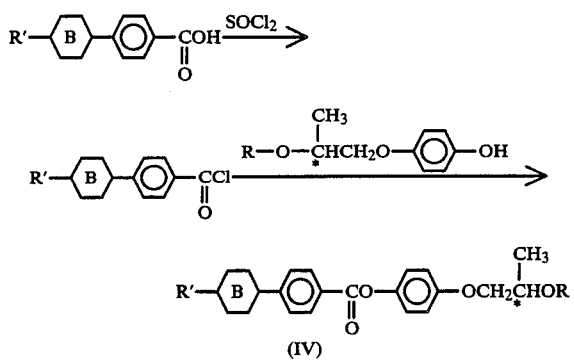

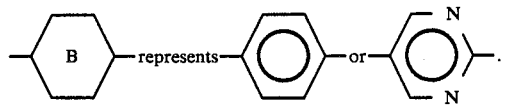

Table 4 shows the phase transition temperatures of the mesomorphic compounds (IV)-(1) in which

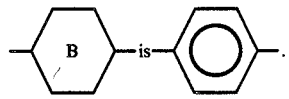

TABLE 4

(IV)-(1)

| R' | R | Phase transition temperature (°C.) | Example |
|---|---|---|---|
| n-C$_{12}$H$_{25}$O— | —n-C$_8$H$_{17}$ | Cryst. $\underset{<50}{\overset{88}{\rightleftarrows}}$ SmC* $\underset{119}{\overset{122}{\rightleftarrows}}$ SmA $\underset{131}{\overset{134}{\rightleftarrows}}$ Iso. | 40 |
| n-C$_8$H$_{17}$O— | —C$_2$H$_5$ | Cryst. $\underset{42}{\overset{53}{\rightleftarrows}}$ Sm2 $\underset{74}{\overset{79}{\rightleftarrows}}$ Sm1 $\underset{97}{\overset{101}{\rightleftarrows}}$ SmC* $\underset{128}{\overset{131}{\rightleftarrows}}$ SmA $\underset{172}{\overset{176}{\rightleftarrows}}$ Iso. | 45 |
| n-C$_8$H$_{17}$O— | —n-C$_3$H$_7$ | Cryst. $\underset{18}{\overset{45}{\rightleftarrows}}$ Sm1 $\underset{66}{\overset{71}{\rightleftarrows}}$ Sm2 $\underset{93}{\overset{96}{\rightleftarrows}}$ SmC* $\underset{123}{\overset{126}{\rightleftarrows}}$ SmA $\underset{165}{\overset{168}{\rightleftarrows}}$ Iso. | 46 |
| n-C$_{10}$H$_{21}$O— | —n-C$_3$H$_7$ | Cryst. $\underset{45}{\overset{84}{\rightleftarrows}}$ Sm1 $\underset{72}{\rightleftarrows}$ SmC* $\underset{141}{\overset{144}{\rightleftarrows}}$ SmA $\underset{159}{\overset{162}{\rightleftarrows}}$ Iso. | 47 |
| n-C$_8$H$_{17}$O— | —n-C$_8$H$_{17}$ | Cryst. $\underset{58}{\overset{67}{\rightleftarrows}}$ Sm1 $\underset{92}{\overset{86}{\rightleftarrows}}$ SmC* $\underset{113}{\overset{116}{\rightleftarrows}}$ SmA $\underset{154}{\overset{158}{\rightleftarrows}}$ Iso. | 48 |
| n-C$_{16}$H$_{33}$O— | —n-C$_{12}$H$_{25}$ | Cryst. $\underset{81}{\overset{100}{\rightleftarrows}}$ SmC* $\underset{116}{\overset{117}{\rightleftarrows}}$ SmA $\underset{118}{\overset{121}{\rightleftarrows}}$ Iso. | 49 |
| n-C$_8$H$_{17}$O— | —n-C$_{12}$H$_{25}$ | Cryst. $\overset{88}{\longrightarrow}$ SmA $\underset{138}{\overset{141}{\rightleftarrows}}$ Iso.; $\underset{56}{\searrow}\underset{85}{\swarrow}$ Sm1 | 50 |
| n-C$_7$H$_{15}$— | —n-C$_8$H$_{17}$ | Cryst. $\underset{\text{below}-20}{\overset{52}{\rightleftarrows}}$ Sm2 $\underset{53}{\overset{58}{\rightleftarrows}}$ Sm1 $\underset{84}{\overset{88}{\rightleftarrows}}$ SmA $\underset{116}{\overset{119}{\rightleftarrows}}$ Iso. | 51 |

In the above formula (IV), R represents a linear, branched or cyclic saturated or unsaturated hydrocarbon groups having 1 to 18 carbon atoms; C* represents an asymmetric carbon atom; R' represents an alkyl group or alkoxy group having 4 to 18 carbon atoms; and Also, the compounds of the formula (IV) wherein

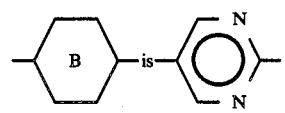

can be obtained according to the following steps.

(IV)-(2)

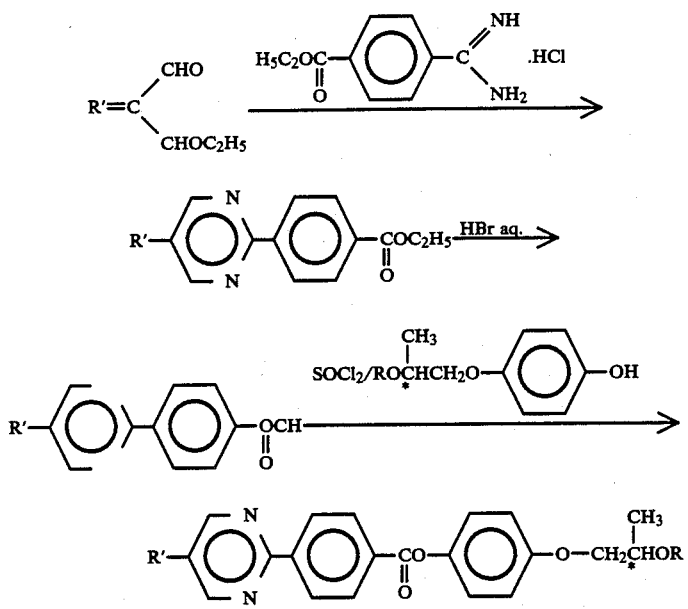

wherein R and R' are the same as defined above.

The liquid crystal composition of the present invention is inclusive of those containing at least one optically active lactic acid derivative of the formula (VI) and also of those containing at least one optically active lactic acid derivative of the formula (IV).

A nematic liquid crystal containing one of the lactic acid derivatives of the present invention as at least one component can be preferably used in the form of a twisted nematic (TN) type cell, whereby generation of reverse domain can be prevented.

Also, the composition containing at least one of the lactic acid derivatives of the present invention and a ferroelectric mesomorphic compound forms a particularly preferable embodiment in the present invention from the standpoint of improvement of the properties of ferroelectric liquid crystal. Typical examples of ferroelectric mesomorphic compounds to be used in this liquid crystal composition are listed in Table 5. It is also preferable practically to control the helical pitch in the smectic phase of cholesteric phase of the composition by adding a cholesteric mesomorphic compound or a mesomorphic compound containing an optically active group to a liquid crystal composition containing the mesomorphic compound having an optically active group of the present invention as at least one component.

In a liquid crystal composition containing the compound of the formula (IV) and the compound of the formula (VI) as at least one component, the compound of the formula (VI) or (IV) should be contained preferably in an amount of 0.1 to 99 wt.%

TABLE 5
Examples of liquid crystals exhibiting chiral smectic phase
(Compound name, structural formula and phase transition point)

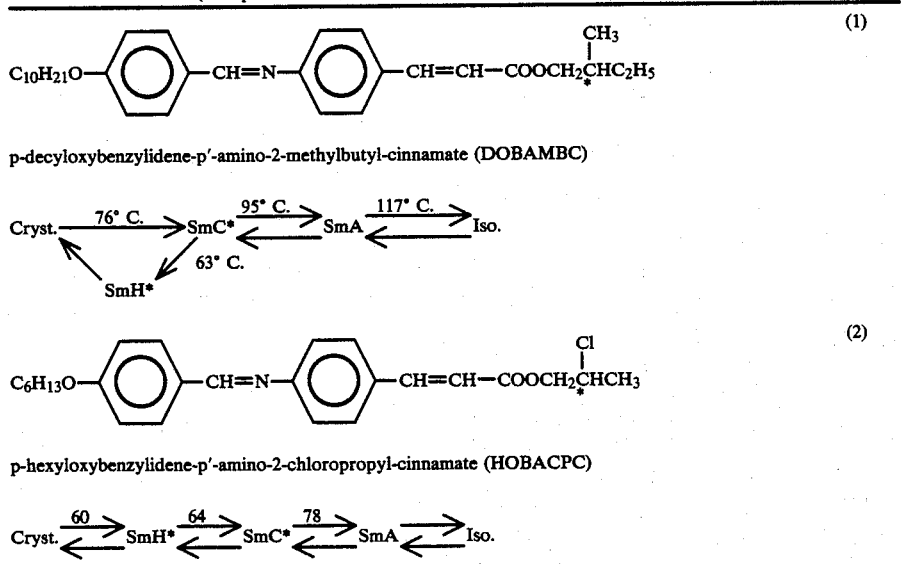

TABLE 5-continued

Examples of liquid crystals exhibiting chiral smectic phase
(Compound name, structural formula and phase transition point)

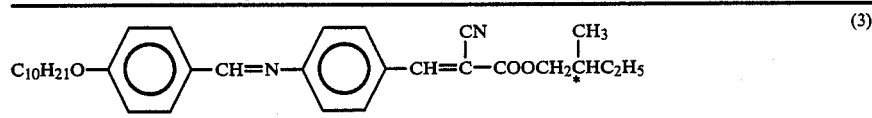 (3)

p-decyloxybenzylidene-p'-amino-2-methylbutyl-α-cyanocinnamate (DOBAMBCC)

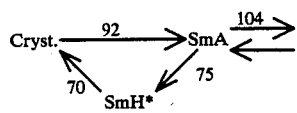

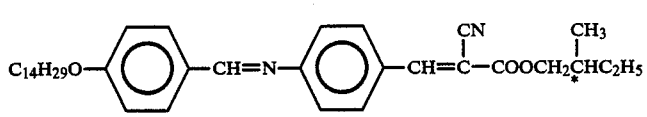 (4)

p-tetradecyloxybenzylidene-p'-amino-2-methylbutyl-α-cyanocinnamate (TDOBAMBCC)

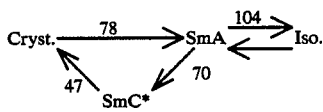

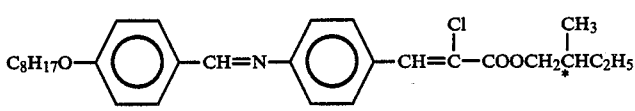 (6)

p-octyloxybenzylidene-p'-amino-2-methylbutyl-α-chlorocinnamate (OOBAMBCC)

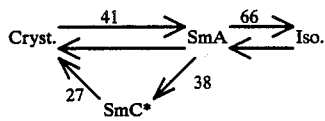

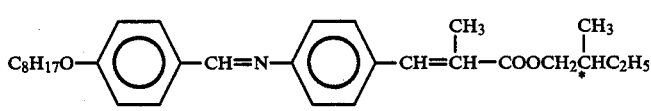 (6)

p-octyloxybenzylidene-p'-amino-2-methylbutyl-α-methylcinnamate

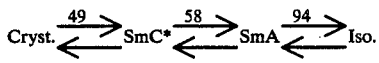

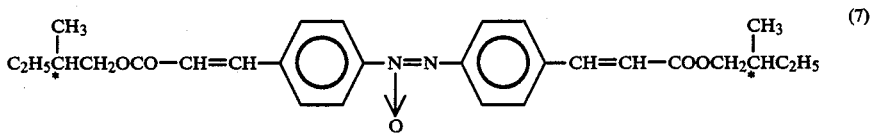 (7)

4,4'-azoxycinnamic acid-bis(2-methylbutyl)ester

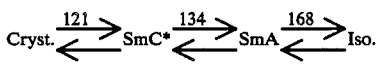

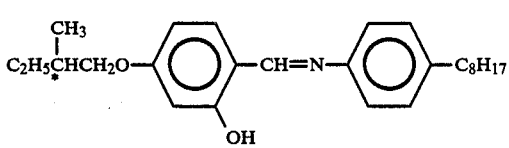 (8)

4-o-(2-methyl)-butylresorcylidene-4'-octylaniline (MBRA 8)

TABLE 5-continued
Examples of liquid crystals exhibiting chiral smectic phase
(Compound name, structural formula and phase transition point)

Cryst. ⇌(28)⇌ SmC* ⇌(55)⇌ SmA ⇌(62)⇌ Iso.

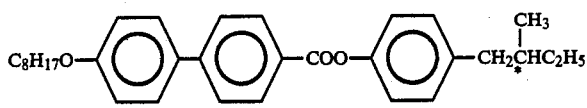

(9)

4-(2'-methylbutyl)phenyl-4'-octyloxybiphenyl-4-carboxylate

Cryst. ⇌(78)⇌ Sm3 ⇌(80)⇌ SmC* ⇌(128.3)⇌ SmA ⇌(171.0)⇌ Ch. ⇌(174.2)⇌ Iso.

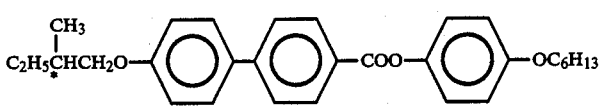

(10)

4-hexyloxyphenyl-4-(2''-methylbutyl)biphenyl-4'-carboxylate

Cryst. ⇌(68.8)⇌ SmC* ⇌(80.2)⇌ Ch. ⇌(163.5)⇌ Iso.

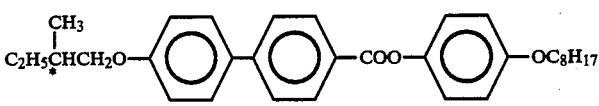

(11)

4-octyloxyphenyl-4-(2''-methylbutyl)biphenyl-4'-carboxylate

Cryst. ⇌(76)⇌ SmC* ⇌(88.6)⇌ Ch. ⇌(155.4)⇌ Iso.

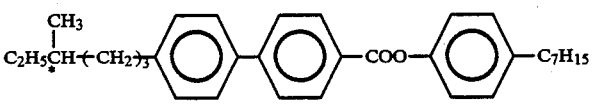

(12)

4-heptylphenyl-4-(4''-methylhexyl)biphenyl-4'-carboxylate

Cryst. ⇌(91.5)⇌ SmC* ⇌(93)⇌ SmA ⇌(112)⇌ Ch. ⇌(131)⇌ Iso.

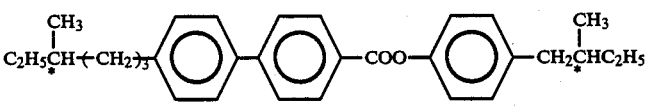

(13)

4-(2''-methylbutyl)phenyl-4-(2''-methylhexyl)biphenyl-4'-carboxylate

Cryst. ⇌(83.4)→ Cholesteric phase →(114)→ Iso.
↓ 81.0
SmC* ←(74.3)— SmA

TABLE 6
Examples of liquid crystals exhibiting cholesteric phase
(compound name, structural formula and phase transition point)

Cholesteryl propionate (A)

Cryst. ⇌(107)⇌ Ch. ⇌(117)⇌ Iso.

Cholesteryl nonanate (B)

TABLE 6-continued
Examples of liquid crystals exhibiting cholesteric phase
(compound name, structural formula and phase transition point)

Cryst. ⇌(78)⇌ Ch. ⇌(92)⇌ Iso.

Cholesteryl palmitate (C)

TABLE 6-continued
Examples of liquid crystals exhibiting cholesteric phase (compound name, structural formula and phase transition point)

Cryst. $\underset{\longleftarrow}{\overset{77}{\longrightarrow}}$ Ch. $\underset{\longleftarrow}{\overset{83}{\longrightarrow}}$ Iso.

Cholesteryl benazonate (D)

Cryst. $\underset{\longleftarrow}{\overset{148}{\longrightarrow}}$ Ch. $\underset{\longleftarrow}{\overset{176}{\longrightarrow}}$ Iso.

$$C_2H_5\underset{*}{\overset{\overset{\displaystyle CH_3}{|}}{C}}HCH_2-\bigcirc-\bigcirc-CN \quad (E)$$

4-(2''-methylbutyl)-4'-cyanobiphenyl

Cryst. $\xrightarrow{4}$ Isotropic phase
$\nwarrow$ $\swarrow$ $-30$
SmA $\xleftarrow{-54}$ Cholesteric phase $$C_2H_5\underset{*}{\overset{\overset{\displaystyle CH_3}{|}}{C}}HCH_2O-\bigcirc-\bigcirc-CN \quad (F)$$

4-(2''-methylbutyloxy)-4'-cyanobiphenyl

Cryst. $\xrightarrow{53.5}$ Isotropic phase
$\nwarrow$ $\swarrow$ 9
Cholesteric phase $$C_2H_5\underset{*}{\overset{\overset{\displaystyle CH_3}{|}}{C}}HCH_2-\bigcirc-COO-\bigcirc-COO-\bigcirc-C_8H_{17} \quad (G)$$

4-octylphenyl-4'-(4-β-methylbutylbenzoyloxy)-benzoate

Cryst. $\underset{\longleftarrow}{\overset{72.6}{\longrightarrow}}$ Ch. $\underset{\longleftarrow}{\overset{154.3}{\longrightarrow}}$ Iso.

$$C_2H_5\underset{*}{\overset{\overset{\displaystyle CH_3}{|}}{C}}HCH_2-\bigcirc-N=CH-\bigcirc-CN \quad (H)$$

4-cyanobenzylidene-4'-(2-methylbutyl)aniline

Cryst. $\xrightarrow{51}$ Iso.
$\nwarrow$ $\swarrow$ 26.5
Ch.

$$C_2H_5\underset{*}{\overset{\overset{\displaystyle CH_3}{|}}{C}}HCH_2-\bigcirc-N=N-\bigcirc-OC_6H_{13} \quad (I)$$

4-(2-methylbutyl)-4'-hexyloxyazobenzene

Cryst. $\underset{\longleftarrow}{\overset{35.9}{\longrightarrow}}$ Ch. $\underset{\longleftarrow}{\overset{58.2}{\longrightarrow}}$ Iso.

$$C_{10}H_{21}O-\bigcirc-COO-\bigcirc-\underset{*}{\overset{\overset{\displaystyle CH_3}{|}}{C}}H_2CHC_2H_5 \quad (J)$$

4-(2-methylbutyl)phenyl-4'-decyloxybenzoate

Cryst. $\underset{\longleftarrow}{\overset{41.8}{\longrightarrow}}$ SmA $\underset{\longleftarrow}{\overset{42.2}{\longrightarrow}}$ Ch. $\underset{\longleftarrow}{\overset{45.3}{\longrightarrow}}$ Iso.

TABLE 6-continued
Examples of liquid crystals exhibiting cholesteric phase (compound name, structural formula and phase transition point)

$$C_2H_5\underset{*}{\overset{\overset{\displaystyle CH_3}{|}}{C}}HCH_2O-\bigcirc-COO-\bigcirc-OC_6H_{13} \quad (K)$$

Cryst. $\underset{\longleftarrow}{\overset{22}{\longrightarrow}}$ Iso.
$\nwarrow$ $\swarrow$ 17
Ch.

$$C_2H_5\underset{*}{\overset{\overset{\displaystyle CH_3}{|}}{C}}HCH_2-\bigcirc-COO-\bigcirc-N=N-\bigcirc-C_7H_{15} \quad (L)$$

Cryst. $\underset{\longleftarrow}{\overset{88}{\longrightarrow}}$ Ch. $\underset{\longleftarrow}{\overset{154}{\longrightarrow}}$ Iso.

Also, in preferable examples of the present invention, liquid crystal compositions containing at least one of the lactic acid derivatives represented by the above formula (IV) and at least one of the lactic acid derivatives represented by the above formula (V) can be used.

According to our study, it has been found that the temperature region for giving the smectic C* phase can be expanded particularly on the lower temperature side and also response speed can be improved to improve the display characteristics by mixing the mesomorphic compounds of the above formula (IV) and the formula (V), as compared with the case of using the respective mesomorphic compounds alone.

Particularly, liquid crystal compositions with particularly excellent characteristics can be obtained in the case of combinations of at least one kind of mesomorphic compounds represented by the following formula (V)-(1), which is the above formula (V) wherein m=1 and n=1:

$$R'-\bigcirc-\bigcirc-COO-\bigcirc-COOCH_2\underset{*}{\overset{\overset{\displaystyle CH_3}{|}}{C}}HOR \quad (V)\text{-}(1)$$

wherein R, R' are the same as in the formula (V), and at least one of the optically active mesomorphic compound, represented by the following formula (IV)-(1), which is the above formula (IV) wherein $-\bigcirc\!\!\!-\!\!B\!\!-\!\!\bigcirc\!\!\!-$ is $-\bigcirc-$:

$$R'-\bigcirc-\bigcirc-COO-\bigcirc-OCH_2\underset{*}{\overset{\overset{\displaystyle CH_3}{|}}{C}}HOR \quad (IV)\text{-}(1)$$

wherein R and R' are the same as in the formula (IV). Particularly, such a liquid composition can form SmC* exhibiting ferroelectricity at low temperature region as described below, and besides excellent high speed response can be exhibited at the time of Sm*.

The liquid crystal composition of the present invention should preferably be formed by mixing 1 to 99% of at least one of the mesomorphic compounds of the above formula (IV) and 99 to 1% of at least one of the mesomorphic compounds of the formula (V).

Also, the liquid crystal composition of the present invention, when combined with ferroelectric liquid crystals shown by the above A-(1) to A-(13) as mentioned above other than the mesomorphic compounds of the above formula (IV) and the above formula (V), can expand the temperature range by lowering the temperature for SmC*.

In such a case, it is preferable to use the total amount of the mesomorphic compound of the above formula (IV) and the mesomorphic compound of the above formula (V) at a ratio of 1 to 99%, particularly 5 to 99% of the liquid composition obtained.

Also, by formulation into a smectic liquid crystal which is not itself chiral as shown by the above formula B-(1) to B-(5), a composition utilizable as ferroelectric liquid crystal can be obtained.

In this case, it is preferable to use the nesomorphic compound of the present invention represented by the formula (V) at a ratio of 1 to 99 wt.%, particularly 5 to 95 wt.% of the liquid crystal composition obtained.

When a device is constituted by using these materials, the device may be supported with a block of copper, etc., in which a heater is embedded in order to realize a temperature condition where the liquid crystal composition assumes, for example, SmC* phase or SmH* phase.

Referring to FIG. 1, there is schematically shown an example of a ferroelectric liquid crystal cell for explanation of the operation thereof. Reference numeral 11a and 11b denote base plates (glass plates) on which a transparent electrode of, e.g., $In_2O_3$, $SnO_2$, ITO (Intium-Tin-Oxide), etc., is disposed respectively. A liquid crystal of a chiral smectic phase such as SmC* or SmH* in which liquid crystal molecular layers 12 are oriented perpendicular to surfaces of the glass plates is hermetically disposed therebetween. A full line 13 shows liquid crystal molecules. Each liquid crystal molecule 13 has a dipole moment ($P_\perp$) 14 in a direction perpendicular to the axis thereof. When a voltage higher than a certain threshold level is applied between electrodes formed on the base plates 11a and 11b, a helical structure of the liquid crystal molecule 13 is loosened or unwound to change the alignment direction of respective liquid crystal molecules 13 so that the dipole moments ($P_\perp$) 14 are all directed in the direction of the electric field. The liquid crystal molecules 13 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 2:
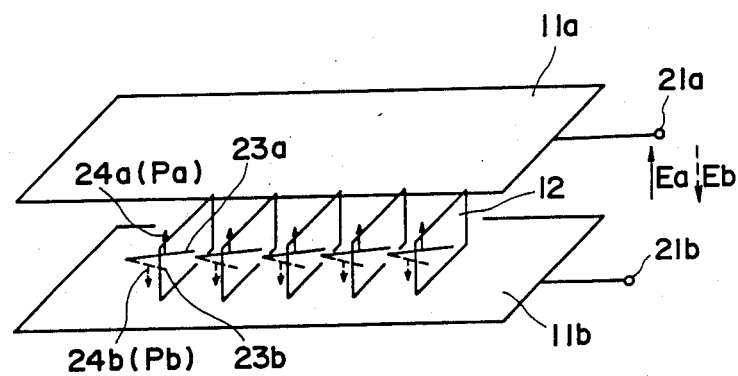

The liquid crystal layer in the liquid crystal device of the present invention may be rendered sufficiently thin (e.g., less than 10μ). As the thickness of the liquid crystal layer is decreased, the helical structure of the liquid crystal molecules is loosened even in the absence of an electric field whereby the dipole moment assumes either of the two states, i.e., Pa in an upper direction 24a or Pb in a lower direction 24b as shown in FIG. 2. When electric field Ea or Eb higher than a certain threshold level and different from each other in polarity as shown in FIG. 2 is applied to a cell having the above-mentioned characteristics, the dipole moment is directed either in the upper direction 24a or in the lower direction 24b depending on the ventor of the electric field Ea or Eb. In correspondence with this, the liquid crystal molecules are oriented to either a first stable state 23a or a second stable state 23b.

When the above-mentioned ferroelectric liquid crystal is used as an optical modulation element, it is possible to obtain two advantages as briefly touched on hereinbefore. First is that the response speed is quite fast. Second is that the orientation of the liquid crystal shows bistability. The second advantage will be further explained, e.g., with reference to FIG. 2. When the electric field Ea is applied to the liquid crystal molecules, they are oriented to the first stable state 23a. This state is kept stable even if the electric field is removed. On the other hand, when the electric field Eb (having a direction opposite to that of the electric field Ea) is applied thereto, the liquid crystal molecules are oriented to the second stable state 23b, whereby the directions of molecules are changed. This state is similarly kept stable even if the electric field is removed. Further, as long as the magnitude of the electric field Ea or Eb being applied is not above a certain threshold value, the liquid crystal molecules are placed in the respective orientation states. In order to effectively realize high response speed and bistability, it is preferable that the thickness of the cell is as thin as possible, generally 0.5 to 20μ, particularly 1 to 5μ.

Next, an example of the method for driving a ferroelectric liquid crystal is explained with reference to FIGS. 3–5.

Figure 3:
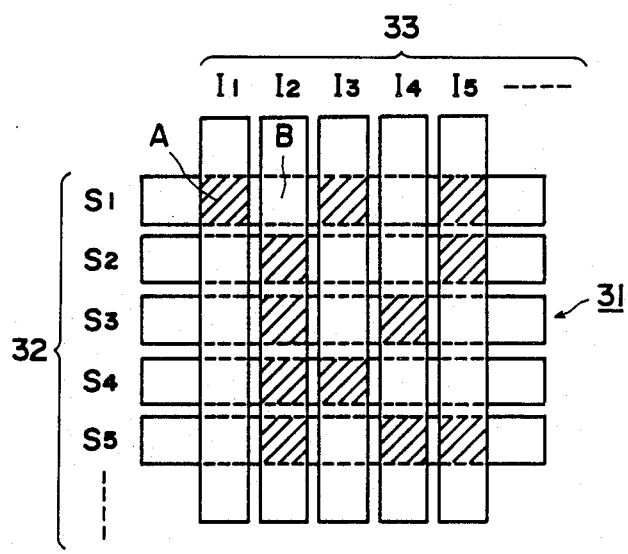
FIG. 3 is a plan view of the matrix electrode structure to be used in the present invention.

Referring to FIG. 3, there is schematically shown an example of cell 31 having a matrix electrode arrangement in which a ferroelectric liquid crystal material (not shown) is interposed between a pair of groups of electrodes oppositely spaced from each other. Reference numerals 32 and 33 respectively denote a group of scanning electrodes to which scanning signals are applied and a group of signal electrodes to which information signals are applied. Referring to FIGS. 4A and 4B, there are respectively shown electric signals applied to a selected scanning electrode $S_1$ and electric signals applied to the other scanning electrodes (non-selected scanning electrodes) $S_2$, $S_3$, $S_4$, .... On the other hand, FIGS. 4C and 4D show electric signals applied to the selected signal electrode $I_1$, $I_3$, $I_5$ and electric signals applied to the non-selected signal electrodes $I_2$, $I_4$, respectively. In FIGS. 4A to 4D and 5A to 5D, the abscissa and the ordinate represent a time and a voltage, respectively. For instance, when discharging a motion picture, the group of scanning electrodes 32 are sequentially and periodically selected. If a threshold voltage for giving a first stable state of the liquid crystal having bistability is referred to as $-V_{th1}$ and a threshold voltage for giving a second state thereof as $+V_{th2}$, an electric signal applied to the selected scanning electrode 32 ($S_1$) is an alternating voltage showing 2 V at a phase (time) $t_1$ and $-2$ V at a phase (time) $t_2$, as shown in FIG. 4A. When such an electric signal having plural phases of mutually different voltages is applied to a selected scanning electrode, an important effect can be obtained that conversion between the first and second stable states corresponding to optically "bright" and "dark" states, respectively, can be quickly caused.

On the other hand, the other scanning electrodes $S_2$–$S_5$ ... are grounded as shown in FIG. 4B. Accordingly, the electric signals appearing thereon show zero volt. On the other hand, an electric signal applied to the selected signal electrode $I_1$, $I_3$, $I_5$ shows V as indicated in FIG. 4C while an electric signal applied to the non-selected signal electrode $I_2$, $I_4$ shows $-V$ as indicated in FIG. 4D. In this instance, the voltage V is set to a desired value which satisfies $V < V_{th2} < 3$ V and $-3$ V $< -V_{th1} < -V$. Voltage waveforms applied to picture elements A and B, for example, among the picture elements shown in FIG. 3 when such electric signals are given are shown in FIGS. 5A and 5B, respectively. Namely, as seen from FIG. 5A, a voltage of 3 V above the threshold level $V_{th2}$ is applied to the ferroelectric liquid crystal at the picture elements A on the selected scanning line at a phase $t_2$. Further, a voltage of $-3$ V exceeding the threshold level $-V_{th1}$ is applied to the ferroelectric liquid crystal at the picture elements B on the same scanning line at a phase $t_1$. Accordingly, depending upon whether a signal electrode is selected or not on a selected scanning electrode line, the orientation of liquid crystal molecules changes. Thus, when a certain signal electrode is selected, the liquid crystal molecules are oriented to the first stable state, while when not selected, oriented to the second stable state.

On the other hand, as shown in FIGS. 5C and 5D, the voltage applied to all the picture elements on the non-selected scanning lines is $+V$ or $-V$, each not exceeding the threshold level. Accordingly, the ferroelectric liquid crystal molecules electrically connected to the respective picture elements on the non-selected scanning lines are placed in the orientations corresponding to signal states produced when they have been last scanned without change in orientation. Namely, when a certain scanning electrode is selected, signals corresponding to one line are written and thus writing of signals corresponding to one frame is completed. The signal state of each picture element can be maintained until the line is subsequently selected. Accordingly, even if the number of scanning lines increases, the duty ratio does not substantially change, resulting in no possibility of lowering in contrast.

Then, a possible problem which can occur when a device as described above is actually driven as a display device, is considered. Referring to FIG. 3, it is assumed that, among the picture elements formed at intersections of the scanning electrodes $S_1$-$S_5$ . . . and the signal electrodes $I_1$-$I_5$, the picture elements with hatching are in the "bright" state and picture elements drawn in white are in the "dark" state. When display states on a signal electrode $I_1$ in FIG. 3 are noted, a picture element (A) on a scanning electrode $S_1$ is in the "bright" state, and the other picture elements (B) are all in the "dark" state. As a driving mode for obtaining such a display plate, FIG. 6 shows an example of the scanning signals, an information signal applied to a signal electrode $I_1$ and a voltage applied to the picture element A in time series.

Figure 6:
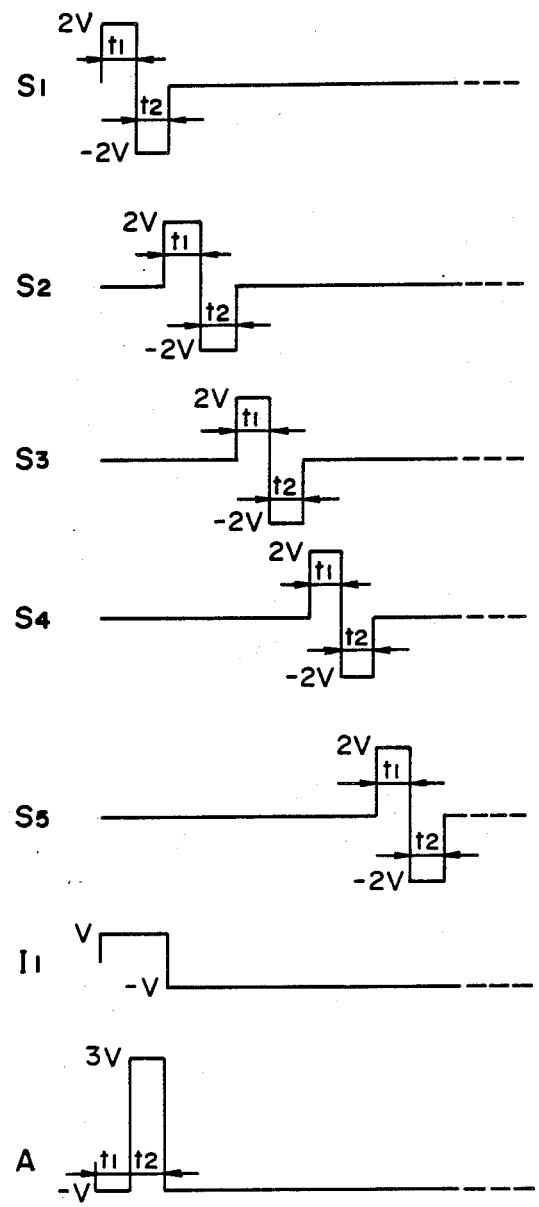
FIG. 6 illustrates a time chart representing signals to be applied on the liquid crystal device of the present invention.

In the driving mode shown in FIG. 6, when a scanning electrode $S_1$ is scanned, a voltage of 3 V exceeding the threshold voltage $V_{th2}$ is applied to the picture element A at time $t_2$, so that the picture element A is oriented or switched to one stable state, i.e., the bright state, regardless of its previous state. After that, during the period when a scanning electrodes $S_2$-$S_5$ . . . are scanned, a voltage of $-V$ is continually applied and the picture element A is expected to keep its "bright" state as the voltage $-V$ does not exceed the threshold voltage $-V_{th1}$. As a matter of actual problem, however, when one direction of signal (one for providing "dark" state in this case) is continually applied to one signal electrode, a reversal of display states can occur especially in a case where a very large number of scanning lines are used and a high speed driving is pursued. Such a reversal phenomenon can be effectively prevented by using the above mentioned specific mesomorphic or liquid crystal compound or a liquid crystal composition containing the same.

Further, in the present invention, for prevention of the reversal phenomenon as mentioned above, it is preferable to form an insulating film formed of an insulating substance on at least one electrode of the opposed electrodes constituting the liquid crystal cell.

The insulating substance to be used in this case is not particularly limited, but rather it is possible to use inorganic insulating substances such as silicon nitrides, silicon nitrides containing hydrogen, silicon carbides, silicon carbides containing hydrogen, silicon oxides, borone nitrides, borone nitrides containing hydrogen, cerium oxides, aluminum oxides, zirconium oxides, titanium oxides or magnesium fluoride, or organic insulating substances such as polyvinyl alcohol, polyimide, polyamideimide, polyesterimide, polyparaxylene, polyester, polycarbonate, polyvinylacetal, polyvinyl chloride, polyvinyl acetate, polyamide, polystyrene, cellulose resin, melamine resin, urea resin, acrylic resin or photoresist resin as the insulating film. These insulating films may have a thickness of 5000 Å or less, preferably 100 Å to 1000 Å, particularly 500 Å to 3000 Å.

The optically active lactic acid derivative according to the present invention can be combined with an intermediate of a functional material having an appropriate intermolecular force and shape without impairing an optical activity and allows arbitrary molecular design. Particularly, by selecting the length of the alkyl group, it is possible to control the kind of and the temperature range for a liquid crystal phase in its mesomorphic state. Further, the liquid crystal composition containing at least one of the optically active lactic acid derivatives and optically active mesomorphic lactic derivatives of the present invention can be used as the chiral nematic liquid crystal, or chiral smectic liquid crystal to effectively improve the performances such as improvement in response speed, prevention of generation of reverse domain through increased spontaneous polarization, control of viscosity, etc.

The present invention is described in more detail about the optically active substances which are lactic acid derivatives of the present invention, mesomorphic lactic acid derivatives and liquid cyrstal compositions by way of examples.

EXAMPLE 1 p-Hydroxybenzoic acid (2-ethoxy)propyl ester 50 g of p-acetyloxybenzoic acid was added to 165 g of $SOCl_2$ and the mixture was heated at 60° C. for 40 minutes. After cooling, the solvent was evaporated to obtain 64.5 g of

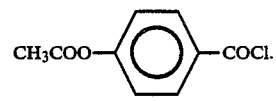

10 g of 2-ethoxypropanol ($C_2H_5OC^*H(CH_3)CH_2OH$) and 11.6 g of N,N-dimethylaniline were dissolved in 20 ml of ether and 22.3 g of

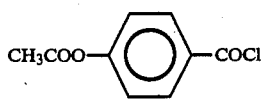

as prepared above was added dropwise to the solution under stirring. Then, the mixture was heated at reflux with stirring for one hour and 30 minutes.

Water was added and the ether layer was separated and purified to obtain p-acetyloxybenzoic acid (2-ethoxy)propyl ester. After methanol was charged into the product, a mixture of methanol: 28% ammonia water=1:1 was added thereto and hydrolysis was carried out by stirring the mixture.

The reaction mixture was extracted with 400 ml of ether, washed with water, dried (with $Na_2SO_4$), and the solvent was evaporated to give 11.5 g of a crude product. Purification through a column of 1 kg of silica gel (moving phase: isopropyl ether:n-hexane=1:1) gave 6.4 g of p-hydroxybenozic acid (2-ethoxy)propyl ester.

For this product, the following IR data were obtained. IR ($cm^{-1}$):
p-Acetyloxybenzoic acid (2-ethoxy)propyl ester: 2980, 2880, 1770, 1720, 1610, 1505, 1375, 1275, 1200, 1160, 1120, 1100.
p-Hydroxybenzoic acid (2-ethoxy)propyl ester: 3310, 2990, 2900, 1720, 1700, 1620, 1600, 1520, 1450, 1390, 1280, 1170, 1100.

EXAMPLE 2 p-Hydroxybenzoic acid (2-propoxy)propyl ester

According to the same procedure as in Example 1, 14.6 g of p-hydroxybenzoic acid (2-propoxy)propyl ester was obtained from 10 g of (2-propoxy)propanol.

For the product, the following IR and NMR data were obtained.
IR: 3370, 3000, 2900, 1720, 1700, 1625, 1610, 1525, 1460, 1395, 1280, 1250, 1180, 1120.
$^1$H-NMR: 0.9–1.8 ppm (8H), 2.3 ppm (1H), 3.4–4.3 ppm (5H), 6.7–8.0 ppm (4H).

EXAMPLES 3–5

According to the same procedure as in Example 1, lactic acid derivatives of the present invention were obtained. The products are as listed in the above Table 1 together with their specific optical rotations.

EXAMPLE 6 p-Hydroxybiphenylcarboxylic acid (2-pentyloxy)propyl ester 9.42 g ($1.68 \times 10^{-1}$ mol) of KOH was dissolved in 30 ml of water, and 15 g ($7.02 \times 10^{-2}$ mol) of p-hydroxybiphenylcarboxylic acid was added dropwise over 10 minutes at room temperature. After the dropwise addition, the crystals precipitated were filtered, and recrystallized from water to obtain 5.9 g of p-acetyloxybiphenylcarboxylic acid (yield: 32.9%).

5.7 g ($2.23 \times 10^{-2}$ mol) of p-acetyloxybiphenylcarboxylic acid was added to 20 g ($1.68 \times 10^{-1}$ mol) of $SOCl_2$ and the mixture was heated at reflux for 3.5 hours. After cooling, the solvent was evaporated to give 7.0 g of p-acetyloxybiphenylcarboxylic acid chloride.

3.25 g ($2.23 \times 10^{-2}$ mol) of 2-pentyloxyhepthanol and 2.69 g ($2.23 \times 10^{-2}$ mol) of N,N-dimethylaniline were dissolved in 10 ml of ether and, under stirring of the solution, 20 ml of a solution of p-acetyloxybiphenylcarboxylic acid chloride as prepared above in toluene was added dropwise over 20 minutes at room temperature. After the dropwise addition, the mixture was heated at reflux for hours.

After completion of the reaction, 50 ml of water was added to dissolve the crystals followed by extraction with ether (30 ml×3). The ether layer was washed with 50 ml of an aqueous 10% $H_2SO_4$ (×4) and with water (×3) and dried over anhydrous sodium sulfate, followed by evaporation of the solvents to give 20.3 g of an oily product. The product was purified by silica gel column chromatography to obtain 8.6 g of p-acetyloxybiphenylcarboxylic acid (2-pentyloxy)propyl ester.

After the p-acetyloxybiphenylcarboxylic acid (2-pentyloxy)propyl ester was diluted with 50 ml of methanol, a mixture of methanol: $NH_4OH$ (28%)=1:1 was added under stirring to carry out hydrolysis. Then, the rection mixture was extracted with anhydrous sodium sulfate (×3), the ether layer was washed with 50 ml of water (×3) and dried over anhydrous sodium sulfate, followed by evaporation of the solvent to obtain an oily product. The product was purified by silica gel chromatography to obtain 2.6 g of p-hydroxybiphenylcarboxylic acid (2-pentyloxy)propyl ester.

For the product, the following IR data were obtained.
IR: 3400, 2950, 2875, 1720, 1700, 1615, 1600, 1450, 1380, 1290, 1260, 1110.

EXAMPLE 9 p'-Decyloxybiphenylcarboxylic acid p''-(2-ethoxypropyloxycarbonyl)phenyl ester 20 ml of $SOCl_2$ was added to 4 g ($1.13 \times 10^{-2}$ mol) of decyloxybiphenylcarboxylic acid, and the mixture was heated at reflux for 3.5 hours. Excessive $SOCl_2$ was evaporated to obtain decyloxybiphenylcarboxylic acid chloride.

The acid chloride obtained was dissolved in 10 ml of toluene and the resultant solution was added dropwise into a solution of 2.35 g ($1.13 \times 10^{-2}$ mol) of optically active p-hydroxybenzoic acid 2-ethoxypropyl ester dissolved in 16 ml of pyridine, and the mixture was left standing at room temperature for 55 minutes and thereafter stirred for 3 hours and 50 minutes.

The reaction mixture was poured into cold water, washed with 6N HCl solution and water, and dried, followed by evaporation of the solvent to give 4.4 g of p'-decyloxybiphenylcarboxylic acid p''-(2-ethoxypropyloxycarbonyl)phenyl ester. Further, after purification by silica gel chromatography, recrystallization gave 1.8 g of a purified product.

For the product, the following IR and NMR data were obtained.
IR: 2940, 2870, 1740, 1610, 1515, 1480, 1395, 1295, 1135, 1090.
$^1$H-NMR: 6.8–8.2 ppm (12H), 3.3–4.3 ppm (7H), 0.8–1.8 ppm (25H).

EXAMPLES 7, 8, 10–15, 19, 20

Mesomorphic compounds were obtained similarly as in Example 9.

The products are as listed in the above Table 2 together with their phase transition temperatures.

EXAMPLE 16

A TN cell (twisted nematic cell) by use of a liquid crystal mixture having 2 parts by weight of the optically active substance of the above Example 5 added to 98 parts by weight of p,p'-pentylazoxybenzene was obtained to provide a nematic phase with greatly reduced reverse domain as compared with the TN cell prepared without addition of this compound.

EXAMPLE 17

Liquid crystal device by use of the mesomorphic compound prepared in Example 9

On a 10×20 mm glass plate subjected to high precision polishing, ITO films of about 1000 Å were provided as electrodes, and further $SiO_2$ of about 1000 Å was vapor deposited thereon according to the ion beam method. The mesomorphic compound prepared in Example 9 was added dropwise on a glass substrate subjected to similar working, and the above glass substrate was superposed thereon as opposed thereto. While pressing the substrate at 160° C. and maintaining the gap between the upper and lower substrates under a polarizing microscope, the both substrates were subjected to parallel movement so as to be displaced from each other, whereby a monodomain oriented horizontally was obtained. The liquid crystal layer thickness at that time was found to be 1.4 μm, and when a pulse of ±10 V were applied at 80° C., switching at about 100 μsec was effected.

EXAMPLE 18

Characteristics of a liquid composition containing the mesomorphic compound prepared in Example 10 as a component A liquid crystal composition comprising 21 wt.% of

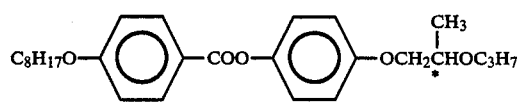

and 79 wt.% of the mesomorphic compound in Example 10 exhibited SmC* at 20°-90° C. in the course of cooling.

EXAMPLE 21

On the respective opposed ITO matrix electrodes in the form of crossing stripes were provided polyimide films having 1000 Å film thickness (formed by coating 5 wt.% N-methylpyrrolidone solution of a polyamic acid resin comprising a condensation product of pyrromellitic anhydride and 4,4'-diaminodiphenyl ether and subjecting it to heating ring closure reaction at 250° C.), and the surfaces of the polyimide films were subjected to rubbing so that they were parallel to each other to prepare a cell with a cell thickness of 1μ.

Subsequently, the following composition A was injected into the above cell according to the vacuum injection method and the cell was sealed. Then, the cell was cooled gradually (1° C./hour) to prepare a liquid crystal cell of SmC*.

Figure 4:
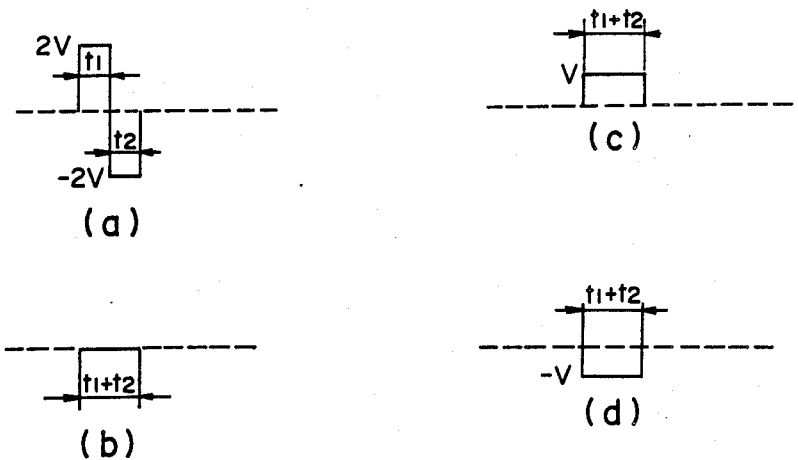
FIGS. 4A-4D illustrate signals to be applied on the matrix electrode.
Figure 5:
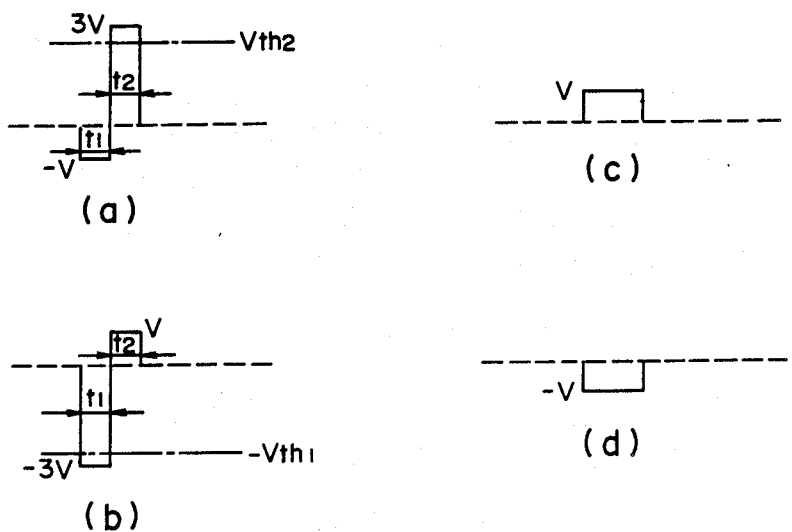
FIGS. 5A to 5D illustrate waveforms of voltage applied between the matrix electrodes.

With a polarizer and an analyzer of crossed nicols being arranged in both sides of the liquid crystal cell, the signals with the waveforms as shown in FIG. 4 and FIG. 5 were applied between the opposed matrix electrodes. During this operation, the scanning signal was one having an alternating waveform of +8 volts and −8 volts as shown in FIG. 4A, while the writing signals were 4 volts and −4 volts, respectively. Also, one frame period was 30 msec.

As the result, even when this liquid crystal device was subjected to the memory driving type time-division driving as described above, a normal motion display could be effected without any reversal of the writing state at all.

COMPARATIVE EXAMPLE 1

A liquid crystal device was made by preparing a liquid crystal B for comparative purpose as shown below, in which the mesomorphic compound represented by the above formula (I) was omitted from the liquid crystal composition A used in making the liquid crystal device of Example 21. When the liquid crystal device was driven in the same manner as described above, normal motion display could not be effected due to occurrence of reversal phenomenon.

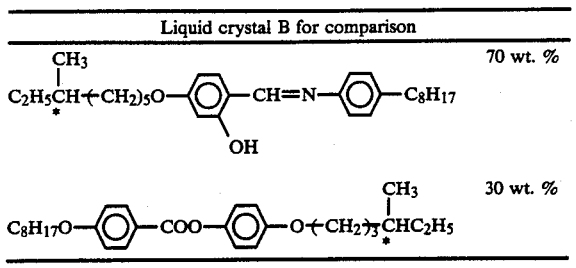

| Liquid crystal B for comparison | |
|---|---|
| (structure 1) | 70 wt. % |
| (structure 2) | 30 wt. % |

EXAMPLE 22 p-Hydroxymono(butoxypropyl)ether (Step 1)

2-Butoxypropanol:

31.5 g of ethyl L-(+)-lactate and 107.3 g of 1-iodobutane were mixed into a four-necked flask, and freshly synthesized Ag$_2$O was added in 2 hours. After left standing at room temperature for 15 hours, the mixture was diluted with 200 ml of ether, filtered and then ether was evaporated. The residue was washed with 100 ml of an aqueous 5% KOH, dried over anhydrous Na$_2$SO$_4$ and subjected to vacuum distillation. The fractions at 110° C./54 mmHg were collected to give 23 g of (−)-ethyl-2-butoxypropionate. Optical rotation $[\alpha]_d^{24°} = -73°$ 2.0 g of LiAlH$_4$ was added to 100 ml of ether and the mixture was stirred for 3 hours, and 12.7 g of (−)-ethyl-2-butoxypropionate was added dropwise thereto. After completion of the dropwise addition, stirring was continued for 15 minutes. Then, 50 ml of water and 50 ml of an aqueous 10% H$_2$SO$_4$ were added. The ether layer was separated and dried over MgSO$_4$. After filtration, ether was evaporated. Yield: 7.4 g, optical rotation $[\alpha]_D^{24°} = +24.4°$.

(Step 2)

2'-Butoxypropyl p-toluene sulfonate:

40 g of dry pyridine and 15.3 g of 2-butoxypropanol were added into a four-necked flask and ice-cooled under stirring, and 35 g of p-toluenesulfonic acid chloride was added little by little to carry out the reaction for 2 hours. Then, the reaction mixture was returned to room temperature and the reaction was further carried out for 16 hours. The reaction product was added into ice-cooled 6% HCl aq. and the mixture was stirred. The mixture was then extracted with benzene and dried over anhydrous Na$_2$SO$_4$. Evaporation of benzene gave (2'-butoxypropyl)p-toluene sulfonate as an oily product. Yield: 33.2 g. The NMR data of this compound are shown below.

7.8–7.3 ppm (q. 4H), 4.0–3.9 ppm (d. 2H),
3.7–3.3 ppm (m. 3H), 2.4 ppm (S, 3H),
1.4–0.8 ppm (m. 10H)

(Step 3)

p-Hydroxymono(2-butoxypropyl)ether:

26 g of hydroquinone and 7.1 g of 85% KOH stirred together with 300 ml of ethanol and 2 ml of water for 7 hours. 15.1 g of 2'-butoxypropyl-p-toluene sulfonate was added, and the mixture was heated at reflux at 60° C. for 3 hours to carry out the reaction for 5 hours, and further the reaction was carried out at room temperature for 11 hours, and then ethanol was evaporated. The residue was added with 500 ml of water and further acidified with HCl aq. After extraction with 500 ml with hexane, the extract was subjected to recrystallization. Yield: 1.9 g (16%), $[\alpha]_D^{26.6°} = -14.1°$ NMR: 6.8 ppm (S. 4H), 4.6 ppm (S. 1H), 3.9–3.5 ppm (m. 5H), 1.6–0.8 ppm (m. 10H)

IR: 3310 cm$^{-1}$, 2950 cm$^{-1}$, 2870 cm$^{-1}$, 1520 cm$^{-1}$, 1445 cm$^{-1}$, 1225 cm$^{-1}$, 1075 cm$^{-1}$, 830 cm$^{-1}$

EXAMPLE 23

Hydroquinone mono(2-pentyloxypropyl)ether (Step 1)

2-Pentyloxypropanol:

In the same manner as in Example 1, 2-pentyloxypropanol was obtained.

(Step 2)

(2'-Pentyloxypropyl) p-toluenesulfonate:

17.6 g of 2'-pentyloxypropanol and 53 g of dry pyridine were added into a four-necked flask and cooled with NaCl-ice. To the cooled mixture was gradually added 35.7 g of p-toluenesulfonic acid chloride. After the reaction was carried out for 3 hours, the mixture was returned to room temperature and the reaction was further continued for 14 hours. The reaction product was thrown into 300 ml of cold water in which a small amount of hydrochloric acid was added. After extraction with benzene, the extract was dried over anhydrous Na$_2$SO$_4$ and benzene was evaporated to give 35.2 g of (2'-pentyloxypropyl) p-toluenesulfonate as oily product.

(Step 3)

Hydroquinone mono(2'-pentyloxypropyl) ether:

16.7 g of hydroquinone, 8.6 g of 85% KOH, 14 g of water and 200 ml of ethanol were added into a four-necked flask, and the reaction was carried out for 13 hours. After elevated in temperature to 50° C., the reaction was further carried out for 3 hours and 30 g of (2'-pentyloxypropyl) p-toluenesulfonate was added dropwise to the reaction mixture and at the temperature elevated to 70° C., the reaction was carried out for 1 hour and then for 3 hours by heating under reflux, and the mixture was left standing at room temperature for 22 hours. After 500 ml of water and a small amount of hydrochloric acid were added to the residue after evaporation of ethanol, the mixture was extracted with 500 ml of hexane. The product after washing twice with water was dried over Na$_2$SO$_4$, recrystallization was effected with hexane.

Optical rotation $[\alpha]_D^{28°} = -13.5°$.

EXAMPLE 24

Hydroquinone mono(2-octyloxypropyl) ether (Step 1)

2-Octyloxypropanol:

In the same manner as in Example 1, 2-octyloxypropanol was obtained.

Optical rotation $[\alpha]_D^{27°} = 16.8°$ (in CHCl$_3$).

(Step 2)

(2'-Octyloxypropyl) p-toluenesulfonate:

53 g of dry pyridine and 22.2 g of 2-octyloxypropanol were added into a four-necked flask and cooled with NaCl-ice. 35.4 g of p-toluenesulfonic acid chloride was added little by little, and after the reaction was carried out for 4 hours, the mixture was left standing at room temperature for 18 hours. The reaction product was added into 500 g of ice-cooled 6% HCl aq. and the mixture was extracted with 500 ml of benzene and dried over anhydrous $Na_2SO_4$, followed by evaporation of benzene, to give 40 g of (2'-octyloxypropyl) p-toluenesulfonate as an oily product.

(Step 3)

Hydroquinone mono(2'-octyloxypropyl) ether 17.0 g of hydroquinone, 11.4 g of 85% KOH, 7.5 ml of water and 200 ml of ethanol were added into a four-necked flask, and after the reaction for 5 hours, the mixture was elevated in temperature to 50° C. and 33 g of (2'-octyloxypropyl) p-toluenesulfonate was added dropwise thereto. After the reaction for 5 hours, the mixture was heated at reflux for 11 hours and thereafter ethanol was evaporated. The residue was added into 600 ml of water and acidified with hydrochloric acid. The mixture was extracted with 500 ml of hexane and the extract was dried over anhydrous $Na_2SO_4$, followed by recrystallization. Yield: 4.2 g (16%). Optical rotation $[\alpha]_D^{26.2°} = -11.3°$.

EXAMPLE 25

Hydroquinone mono(2'-dodecyloxypropyl)ether (Step 1)

2-Dodecyloxypropanol:

47.0 g of ethyl L-(+)-lactate and 88.4 g of 1-iodododecane were added into a flask and mixed under nitrogen gas stream. 42.1 g of freshly synthesized $Ag_2O$ was added in 3 hours. After the mixture was left standing at room temperature for 50 hours, it was heated on a water bath at 60°-70° C. for 4 hours. The mixture was diluted with 200 ml of ether, subjected to filtration and then ether was evaporated. The residue was washed with 100 ml of aqueous 5% KOH, then dried over anhydrous $Na_2SO_4$ and subjected to vacuum distillation. The fractions of 169° C./9 mmHg were collected to obtain 22 g of (−)-ethyl-2-dodecyloxypropionate. Optical rotation $[\alpha]_D^{23°} = -42°$.

1.9 g of $LiAlH_4$ was added to 70 ml ether and the mixture was stirred for 4 hours. To the resultant mixture was added dropwise a solution of 16.5 g of (−)-ethyl-2-dodecyloxypropionate dissolved in 10 ml of ether. After completion of the dropwise addition, stirring was continued for 15 minutes. 50 ml of deionized water was added, and further 50 ml of 10% aqueous $H_2SO_4$ was added. The ether layer was separated and dried over anhydrous $MgSO_4$. After drying, ether was evaporated. Yield: 12.0 g. Optical rotation $[\alpha]_D^{26°} = +11.1°$.

IR: 3430 cm$^{-1}$, 2930 cm$^{-1}$, 2850 cm$^{-1}$, 1470 cm$^{-1}$, 1380 cm$^{-1}$, 1100 cm$^{-1}$, 1050 cm$^{-1}$.

(Step 2)

(2-Dodecyloxypropyl) p-toluenesulfonate 6.6 g of 2-dodecyloxypropanol and 20 ml of dry pyridine were mixed and cooled with NaCl-ice. 8.0 g of p-toluenesulfonic acid chloride was added little by little, and the reaction was continued for 9 hours. The reaction mixture returned to room temperature was mixed with a mixture of 30 ml of conc. hydrochloric acid added to 110 g of water, and the mixture was extracted with benzene and dried over anhydrous $Na_2SO_4$. Evaporation of benzene gave (2-dodecyloxypropyl) p-toluenesulfonate as an oily product. Yield: 10.7 g.

(Step 3)

Hydroquinone mono(2'-dodecyloxypropyl) ether 11.1 g of hydroquinone, 3.1 g of 85% KOH and 100 ml of ethanol were mixed and the reaction was carried out for 2.5 hours. 10.7 g of (2'-dodecyloxypropyl) p-toluenesulfonate was added dropwise and after the reaction was carried out at 60° C. for 3 hours and by heating under reflux for 7.0 hours, ethanol was evaporated. The residue was diluted with 200 ml of water, acidified with a small amount of hydrochloric acid and then extracted with 500 ml of hexane, followed by recrystallization. Yield: 1.1 g (12%). Optical rotation $[\alpha]_D^{26°} = -8.6°$.

EXAMPLES 26-39

The procedures similar to Example 25 were performed to synthesize the compounds as listed in Table 3 described hereinbefore. Optical rotations are also shown in Table 3.

EXAMPLE 40

4(2'-Octyloxypropoxy)phenyl-4'-dodecyloxybiphenyl-4-carboxylate 85 g of 4-oxybiphenyl was dissolved in 1.5 liter of 1.5 N-NaOH solution and reacted with 2 mols of methylsulfuric acid so that the temperature did not exceed 60° C., and then the temperature was elevated to 70° C. in 30 minutes. Recrystallization from ethanol gave 4-methoxybiphenyl crystals melting at 80.5° C. (yield 90-95%).

After 11.5 g of 4-methoxybiphenyl was dissolved in 75 ml of carbon disulfide just distilled, the solution was cooled to 0°-2° C. and 9.5 g of anhydrous aluminum chloride was promptly added under stirring. Then, 5.8 ml of acetyl chloride was added dropwise over 5-10 minutes. Subsequently, the temperature was gradually elevated to 35° C. to complete the reaction. After refluxing for about 45 minutes, the mixture was cooled and decomposed with addition of 60 ml of cold conc. hydrochloric acid. After the solvent was removed by blowing steam into the solvent, the residue was quenched under sufficient stirring to give pink crystals tinted with brown color. After extracted twice with 40 ml of ether for removal of the 3-ketone isomer, the product was recrystallized from isopropyl alcohol to obtain 4-acetyl-4'-methoxybiphenyl with a melting point of 156.5° C. and at a yield of 60-77%.

A solution of 18 g of 4-acetyl-4'-methoxybiphenyl in 285 ml of dioxane was oxidized with a dilute sodium hypobromite. Recrystallization from ethanol and acetic acid gave 4'-methoxybiphenyl-4-carboxylic acid melting at 285° C.

25 g of 4'-methoxybiphenyl-4-carboxylic acid, 1 liter of acetic acid and 200 ml of 48% hydrobromic acid were refluxed for 12-14 hours and then the mixture was thrown into 2.5 liter of water. After cooling, the crystals were collected to obtain 4-hydroxybiphenylcarboxylic acid with a melting point of 288°-291° C. and at a yield of 90-95%.

0.01 mol of p-oxybiphenylcarboxylic acid and 0.02 mol of potassium hydroxide were dissolved in 300 ml of alcohol and 30 ml of water. Then, 1.2 mol of n-dodecylbromide was added, and the mixture was refluxed for 12 hours. A 10% solution containing 1.12 g of potassium hydroxide was refluxed for 2 hours to carry out hydrolysis. Recrystallization was effected from ethanol and glacial acetic acid.

4'-2-Dodecyloxybiphenylcarboxylic acid was obtained.

40 ml of thionyl chloride was added to 1.23 g of 4'-n-dodecyloxybiphenylcarboxylic acid and the mixture was heated at reflux for 5 hours. Thionyl chloride was evaporated, and further 40 ml of dry benzene was added, which was again evaporated. 40 ml of dry pyridine was added and, after cooling, a solution of 1.37 g of hydroquinone mono(2'-dodecyloxypropyl) ether in 36 ml of dry benzene was added dropwise. After stirring for 16 hours, the mixture was heated at reflux for 4 hours. After cooling, 150 ml of 10% HCl aq. was added, and the mixture was extracted with benzene, washed with water, aqueous $Na_2CO_3$ and water, followed by drying over anhydrous $Na_2SO_4$. After evaporation of benzene, the residue was recrystallized from ethanol.

IR: 2920 $cm^{-1}$, 2840 $cm^{-1}$, 1730 $cm^{-1}$,
1600 $cm^{-1}$, 1520 $cm^{-1}$, 1290 $cm^{-1}$,
1200 $cm^{-1}$, 1085 $cm^{-1}$, 765 $cm^{-1}$.

NMR: 8.3-6.9 ppm (12H), 4.0-3.5 ppm (7H), 1.6-0.9 ppm (41H)

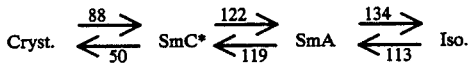

EXAMPLE 41

4-(5-Heptylpyrimidine-2-yl)benzoic acid (2'-butoxypropyloxy)phenyl ester 25 g of 2-heptylmalondialdehyde tetraethylacetal was stirred together with 40 ml of ethanol, 4 ml of water and 3 drops of conc. sulfuric acid at 50° C. for 20 hours, and the mixture was diluted with ether. After unaltered 2-heptylmalondialdehyde tetraethylacetal was removed with dil. aqueous $Na_2CO_3$, ether was evaporated. 15 g of the 2-heptyl-3-ethoxyacrolein thus obtained, 17 g of 4-amidinobenzoic acid methyl ester hydrochloride, and 8.0 g of sodium methylate were stirred in 150 ml of methanol under nitrogen gas stream at room temperature overnight. The precipitate was separated by filtration, and washed with water, methanol and ether. 3.9 g of methyl-4-(5-heptylpyridin-2-yl) benzoate was added to 40.6 g of an aqueous 47% HBr, and the mixture was refluxed under stirring for 5 hours, and then left standing at room temperature for 17 hours. Water was added and the crystal was separated by filtration, recrystallized from ethanol and filtered, followed by drying.

1.28 g of the obtained 4-(5-heptylpyridin-2-yl)benzoic acid was added to 40ml of thionyl chloride, and the mixture was refluxed under stirring for 2 hours. Thionyl chloride was evaporated, 40 ml of dry pyridine was added, and the mixture was stirred under ice-cooling. To this mixture was added dropwise a solution of 1.34 g of hydroquinone mono(2'-butoxypropyl)ether in 30 ml of dry benzene.

After the reaction for 2 hours, the mixture was refluxed for 2 hours, cooled and then added with 100 ml of dil. hydrochloric acid and extracted with benzene. The extract was washed twice with water, dried over anhydrous $Na_2SO_4$ and benzene was evaporated, followed by recrystallization from ethanol.

IR: 2920 $cm^{-1}$, 2850 $cm^{-1}$, 1735 $cm^{-1}$,
1950 $cm^{-1}$, 1480 $cm^{-1}$, 1435 $cm^{-1}$,
1260 $cm^{-1}$, 1190 $cm^{-1}$, 1080 $cm^{-1}$

NMR 8.7 ppm (S, 2H), 8.6-8.3 ppm (q, 4H), 7.2-6.8 ppm (m, 4H), 3.9 ppm (m, 3H), 3.6-3.4 ppm (t, 2H), 2.7-2.6 ppm (t, 2H), 1.5-0.9 ppm (m, 23H).

EXAMPLE 42

A twisted nematic (TN) cell prepared by use of a liquid crystal mixture comprising 1 part by weight of (−)-hydroquinone mono(2'-dodecyloxypropyl) ether of Example 25 of the present invention added to 99 parts by weight of Rikson GR-63 (biphenyl liquid crystal mixture produced by Chisso K.K.) was observed to provide a nematic phase with greatly reduced reverse domain as compared with a TN cell prepared without addition of this compound.

EXAMPLE 43

A twisted nematic (TN) cell prepared by use of a liquid crystal mixture compising 2 parts by weight of 4-(2'-octyloxypropoxy)phenyl-4'-dodecyloxybiphenyl-4-carboxylate of Example 40 of the present invention added to 98 parts by weight of Rikson GR-63 (biphenyl liquid crystal mixture produced by Chisso K.K.) was observed to provide a nematic phase with greatly reduced reverse domain as compared with a TN cell prepared without addition of this compound.

EXAMPLE 44

While the liquid crystal composition in Table 7 exhibits SmC* phase at 33°–50° C., the liquid composition obtained by adding 19.1 wt.% of the compound in Example 40 of the present invention to the liquid composition in Table 7 exhibited SmC* phase at 18°–71° C. Thus, the temperature range could be expanded considerably.

TABLE 7

| | |
|---|---|
| $C_8H_{17}O$—◯—COO—◯—OCH$_2$ĊHC$_2$H$_5$ with CH$_3$ | 80 wt. % |
| $C_8H_{17}O$—◯—OC(=O)—◯—◯—CH$_2$ĊHC$_2$H$_5$ with CH$_3$ | 20 wt. % |

EXAMPLE 52

On the respective opposed ITO matrix electrodes in the form of cross stripes were provided polyimide films having 1000 Å film thickness (formed by coating 5 wt.% N-methylpyrrolidone solution of a polyamic acid resin comprising a condensation product of pyrromellitic anhydride and 4,4'-diaminodiphenyl ether and subjecting it to heating ring closure reaction at 250° C.), and the surfaces of the polyimide films were subjected to rubbing so that they were parallel to each other to prepare a cell with a cell thickness of 1μ.

Subsequently, the following composition A was injected into the above cell according to the vacuum injection method and the cell was sealed. Then, the cell was cooled gradually (1° C./hour) to prepare a liquid crystal cell of SmC*.

| Liquid crystal composition A | |
|---|---|
| $C_8H_{17}O-\bigcirc-COO-\bigcirc-OCH_2\overset{*}{C}H(CH_3)C_2H_5$ | 65 wt. % |
| $C_8H_{17}O-\bigcirc-OCO-\bigcirc-OCH_2\overset{*}{C}H(CH_3)C_2H_5$ | 16 wt. % |
| $C_{12}H_{25}O-\bigcirc-\bigcirc-COO-\bigcirc-OCH_2\overset{*}{C}H(CH_3)OC_8H_{17}$ | 14 wt. % |
| $C_8H_{17}-\bigcirc-\bigcirc-COO-\bigcirc-OCH_2\overset{*}{C}H(CH_3)OC_8H_{17}$ | 5 wt. % |

With a polarizer and an analyzer of crossed nicols being arranged on both sides of the liquid crystal cell, the signals with the waveforms as shown in FIG. 4 and FIG. 5 were applied between the opposed matrix electrodes. During this operation, the scanning signal was one having an alternating waveform of +8 volts and −8 volts as shown in FIG. 4A, while the writing signals were 4 volts and −4 volts, respectively. Also, one frame period was made 30 msec.

As the result, even when this liquid crystal device was subjected to the memory driving type time-division driving as described above, a normal motion display could be obtained without any reversal of the writing state at all.

COMPARATIVE EXAMPLE 2

A liquid crystal device was made by preparing a liquid crystal composition as shown in Table 7 in which the mesomorphic compounds represented by the above formula (IV) was omitted from the liquid crystal composition A used in making the liquid crystal device of Example 52. When the liquid crystal device was driven in the same manner as described above, normal motion display could not be effected due to occurrence of reversal phenomenon.

The optically active lactic acid derivative according to the present invention can be combined with an intermediate of a functional material having an appropriate intermolecular force and shape without impairing an optical activity and allows arbitrary molecular design. Particularly, by selecting the length of the alkyl group, it is possible to control the kind of and the temperature range for a liquid crystal phase in its mesomorphic state. Further, the liquid crystal composition containing at least one of the optically active lactic acid derivatives and optically active mesomorphic lactic derivatives of the present invention can be used as a chiral nematic liquid crystal, or chiral smectic liquid crystal to effectively improve the performance.

EXAMPLE 53

Figures 7, 8:
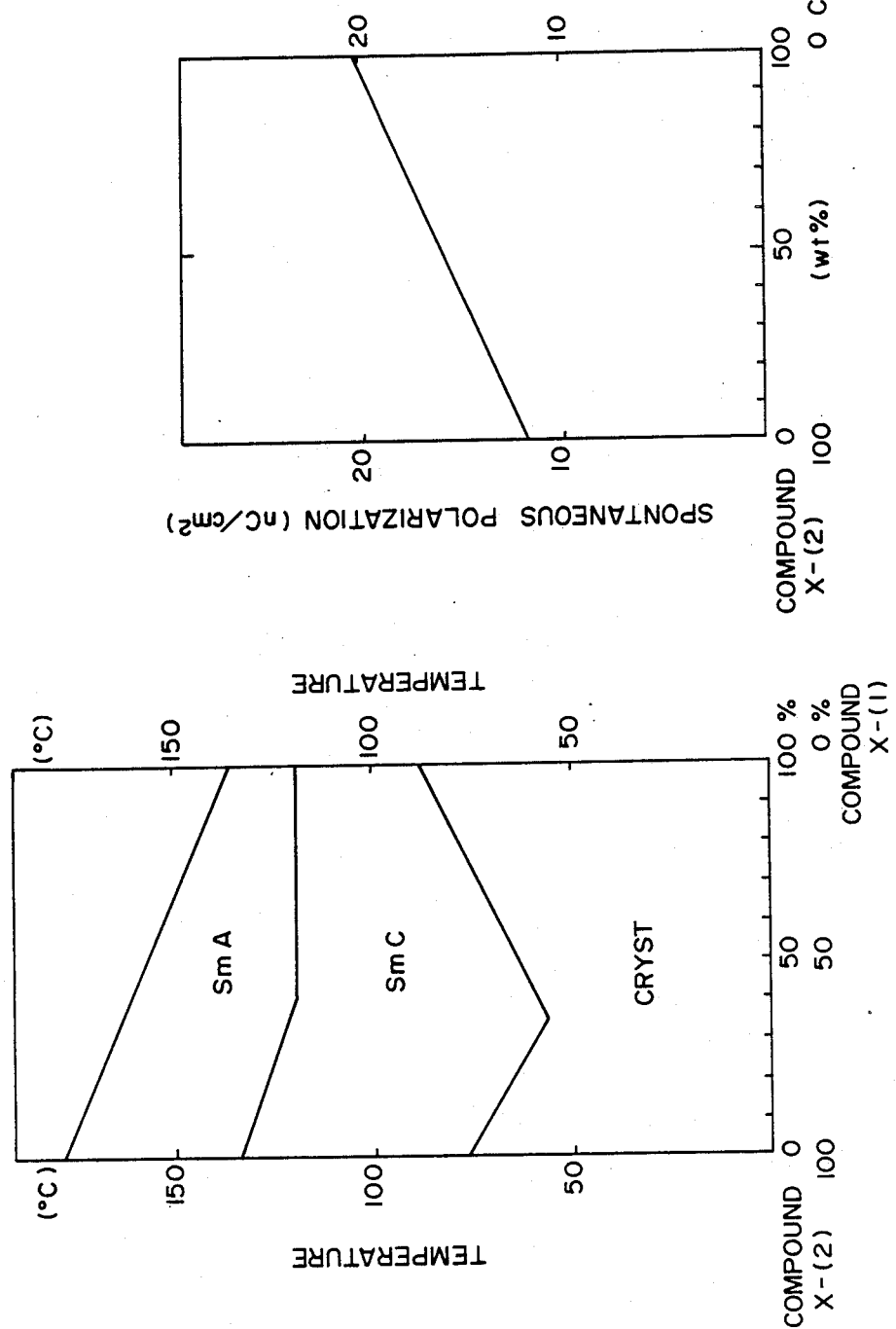
FIG. 7 is a phase diagram showing the change in phase transfer temperature with the composition by mixing of the mesomorphic compound X-(1) and the mesomorphic compound X-(2) according to Example 53.
FIG. 8 is a graph of relationship between spontaneous polarization and composition.

Two kinds of mesomorphic compounds X-(1) and X-(2) obtained in the above Examples 9 and 40 were mixed. FIG. 7 shows the change in phase transition temperature (temperature elevation process) of the liquid crystal composition thus obtained as a phase diagram. Also, FIG. 8 shows the change in spontaneous polarization of the composition with the composition.

Spontaneous polarization was measured by "Direct Method with Triangular Waves for Measuring Spontaneous Polarization in Ferroelectric Liquid Crystal", as described by K. Miyasato et al. (Jap. J. Appl. Phys. 22, No. 10, L661 (1983)).

As is apparent from FIG. 7, the temperature range of SmC* can be greatly expanded by mixing the mesomorphic compounds X-(1) and X-(2) at a ratio of 1:2, whereby SmC* can be maintained relatively stably even at a supercooled temperature.

For the above liquid crystal composition (1:2 mixture) response speed was measured. That is, with the above liquid crystal composition sandwiched between a pair or electrode substrates applied with rubbing treatment on the polyimide coating covering the electrodes, and the liquid crystal layer thickness being made 2 μm, the response speed was measured by detecting the optical response under crossed nicols by application of a voltage of 10 V as a peak-to-peak voltage. The results are shown in Table 8 below.

TABLE 8

| | Compound X-(1) | Compound X-(2) | X-(1) + X-(2) (1:2) |
|---|---|---|---|
| Measurement temperature | 80° C. | 80° C. | 75° C. |
| Response speed | 350 μsec | 280 μsec | 250 μsec |

As can be seen from the above results, the mixed liquid crystal composition according to the present invention (X-(1):X-(2) (1:2)) is improved in response speed as compared with single mesomorphic compounds, with faster response even at a lower temperature.

EXAMPLE 54

A liquid crystal composition was obtained by mixing the mesomorphic compound X-(1) and the mesomorphic compound X-(3) prepared in Example 47 at a ratio of 28:72. This liquid crystal composition was found to exhibit SmC* phase at 70°–137° C. in the temperature elevation process. By use of this composition, a device was prepared in the same manner as in Example 53 and response speed was measured at a temperature of 80° C. under entirely the same conditions to be 210 μsec., thus being improved in characteristics as compared with the case of using a single mesomorphic compound (the response speed of the single mesomorphic compound with the No. X-(3) at 100° C. was 270 μsec).

EXAMPLE 55

A liquid crystal composition was obtained by mixing the mesomorphic compound X-(4) prepared in the above Example 13 and the above mesomorphic compound X-(2) at a ratio of 30:70. It was found to have SmC* phase at 55 to 95° C. A device was prepared in the same manner as in Example 53 by use of this liquid crystal composition, and the response speed was measured at 80° C. under entirely the same condition to be 200 μsec., thus being improved in response speed.

EXAMPLE 56

A liquid crystal composition was obtained by mixing the mesomorphic compounds X-(1), X-(2) and the mesomorphic compound X-(5) prepared in the above Example 19 at ratios of 31:62:7. By use of this composition, a device was prepared similarly as in Example 53, and the response speed was measured at 70° C. under entirely the same conditions to be 190 μsec. Thus, the response speed was found to be improved as compared with the case of employing the mesomorphic compound X-(5).

As can be seen from the above Examples, by mixing the mesomorphic compounds represented by the formula (IV) and the formula (V) according to the present invention, liquid crystal compositions with expanded smectic phase toward the lower temperature side and having excellent characteristic not found in single mesomorphic compounds such as improved response speed, as compared with the respective single mesomorphic compounds, can be obtained.

What is claimed is:

1. An optically active lactic acid derivative represented by the following formula (V):

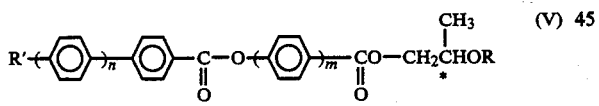

wherein R represents a linear, saturated hydrocarbon group having 1 to 18 carbon atoms; C* represents an asymmetric carbon atom; R' represents a linear alkyl group or alkoxy group having 5 to 16 carbon atoms; m is 1 or 2; n is 0 or 1 and m+n=1 or 2.

2. A lactic acid derivative according to claim 1, wherein said R has 4 to 16 carbon atoms.

3. A lactic acid derivative according to claim 1, wherein, in the formula (V), m is 1, n is 1, R is C$_2$H$_5$—, and R' is n—C$_8$H$_{17}$O—.

4. A lactic acid derivative according to claim 1, wherein, in the formula (V), m is 1, n is 1, R is n—C$_3$H$_7$—, and R' is n—C$_8$H$_{17}$O—.

5. A lactic acid derivative according to claim 1, wherein, in the formula (V), m is 1, n is 1, R is C$_2$H$_5$—, and R' is n—C$_{10}$H$_{21}$O—.

6. A lactic acid derivative according to claim 1, wherein, in the formula (V), m is 1, n is 1, R is n—C$_3$H$_7$—, and R' is n—C$_{10}$H$_{21}$O—.

7. A lactic acid derivative according to claim 1, wherein, in the formula (V), m is 1, n is 1, R is n—C$_{12}$H$_{25}$, and R' is n—C$_5$H$_{11}$O—.

8. A lactic acid derivative according to claim 1, wherein, in the formula (V), m is 1, m is 1, n is 1, R is n—C$_{12}$H$_{25}$—, and R' is n—C$_{12}$H$_{25}$O—.

9. A lactic acid derivative according to claim 1, wherein, in the formula (V), m is 1, n is 1, R is n—C$_8$H$_{17}$—, and R' is n—C$_8$H$_{17}$O—.

10. A lactic acid derivative according to claim 1, wherein, in the formula (V), m is 1, n is 1, R is n—C$_5$H$_{11}$—, and R' is n—C$_{16}$H$_{33}$O—.

11. A lactic acid derivative according to claim 1, wherein, in the formula (V), m is 1, n is 1, R is n—C$_8$H$_{17}$—, and R' is n—C$_7$H$_{15}$O—.

12. A lactic acid derivative according of claim 1, wherein, in the formula (V), m is 1, n is 0, R is n—C$_6$H$_{11}$, and R' is n—C$_{12}$H$_{25}$O—.

13. A lactic acid derivative according to claim 1, wherein, in the formula (V), m is 2, n is 0, R is n—C$_5$H$_{11}$—, and R' is n—C$_{10}$H$_{21}$O—.

14. A chiral smectic liquid crystal composition consisting of at least two compounds and containing at least one compound represented by the following formula (V):

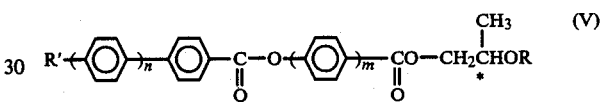

wherein R represents a linear, saturated hydrocarbon group having 1 to 18 carbon atoms; C* represents an asymmetric carbon atom; R' represents a linear alkyl group or alkoxy group having 5 to 16 carbon atoms; m is 1 or 2; n is 0 or 1 and m+n=1 or 2.

15. A liquid composition according to claim 14, wherein said R has 4 to 16 carbon atoms.

16. A liquid crystal composition, which comprises containing at least one of optically active lactic acid derivatives represented by the formula (IV):

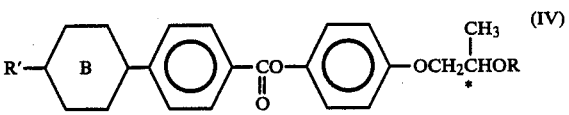

wherein R represents a linear, saturated hydrocarbon group having 1 to 18 carbon atoms; C* represents an asymmetric carbon atom; R' represents an alkyl group or alkoxy group having 4 to 18 carbon atoms; and

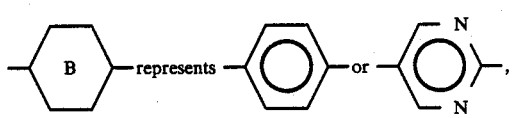

and at least one of optically active lactic acid derivatives represented by the following formula (V):

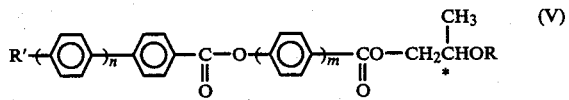

wherein R represents a linear, saturated hydrocarbon group having 1 to 18 carbon atoms; C* represents an asymmetric carbon atom; R' represents a linear alkyl group or alkoxy group having 5 to 16 carbon atoms; m is 1 or 2; n is 0 or 1 and m+n=1 or 2.

17. A liquid crystal composition according to claim 16, wherein said R has 4 to 16 carbon atoms.

18. A liquid crystal composition comprising at least one optically active lactic acid derivative represented by the formula

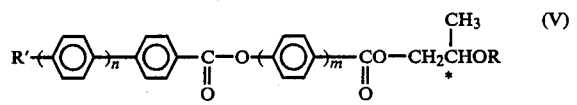

wherein R is a linear alkyl group having 1 to 18 carbon atoms; C* is an asymmetric carbon atom; R' is a linear alkyl group or an alkoxy group having 5 to 16 carbon atoms, m is 1 or 2; n is 0 or 1 and m+n=1 or 2.

19. A liquid crystal device comprising a pair of oppositely spaced electrodes and a liquid crystal composition disposed between the oppositely spaced electrodes; said liquid crystal composition comprising at least one optically active lactic acid derivative represented by the formula

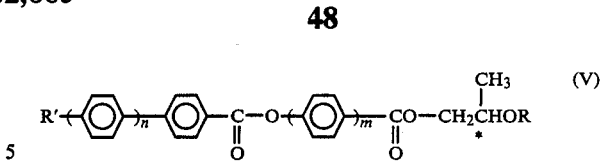

wherein R is a linear alkyl group having 1 to 18 carbon atoms; C* is an asymmetric carbon atom; R' is a linear alkyl group or an alkoxy group having 5 to 16 carbon atoms, m is 1 or 2; n is 0 or 1 and m+n=1 or 2.

20. A ferroelectric liquid crystal device, which comprises a pair or oppositely spaced electrodes and a chiral smectic liquid crystal composition disposed between the oppositely spaced electrodes; said chiral smectic liquid crystal composition consisting of at least two compounds and containing at least one compound represented by the following formula (V):

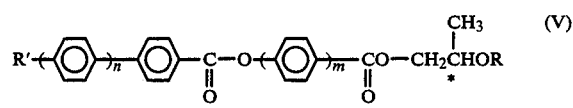

wherein R represents a linear, saturated hydrocarbon group having 1 to 18 carbon atoms; C* represents an asymmetric carbon atom; R' represents a linear alkyl group or alkoxy group having 5 to 16 carbon atoms; m is 1 or 2; and n is 0 or 1 and m+n=1 or 2.

* * * * *

UNITED STATES PATENT AND TRADEMARK OFFICE
CERTIFICATE OF CORRECTION

PATENT NO. : 4,882,085
DATED : November 21, 1989
INVENTOR(S) : KAZUO YOSHINAGA ET AL.   Page 1 of 2

It is certified that error appears in the above-identified patent and that said Letters Patent is hereby corrected as shown below:

COLUMN 4

Line 37, "$CH_3$" should read --$CH_3$    (III)--.

COLUMN 6

Line 61, " 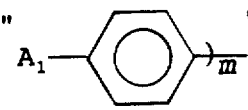 " should read -- 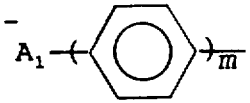 --.

COLUMN 27

Line 7, "Cholesteryl benazonate" should read --Cholesteryl benzonate--.

COLUMN 29

Line 17, "nesomorphic" should read --mesomorphic--.

COLUMN 46

Line 5, "m is 1," (second occurrence) should be deleted.

UNITED STATES PATENT AND TRADEMARK OFFICE
CERTIFICATE OF CORRECTION

PATENT NO. : 4,882,085
DATED : November 21, 1989
INVENTOR(S) : KAZUO YOSHINAGA ET AL.   Page 2 of 2

It is certified that error appears in the above-identified patent and that said Letters Patent is hereby corrected as shown below:

COLUMN 47

Line 11, "the formula" should read
--the following formula (V):--.
Line 29, "the formula" should read
--the following formula (V):--.

Signed and Sealed this

Tenth Day of May, 1994

Attest:

BRUCE LEHMAN

Attesting Officer   Commissioner of Patents and Trademarks